US007919264B2

(12) United States Patent
Maksymowych et al.

(10) Patent No.: US 7,919,264 B2
(45) Date of Patent: Apr. 5, 2011

(54) METHODS AND COMPOSITIONS FOR DETERMINING THE EFFICACY OF A TREATMENT FOR ANKYLOSING SPONDYLITIS USING BIOMARKERS

(75) Inventors: Walter P. Maksymowych, Edmonton (CA); Robert L. Wong, Basking Ridge, NJ (US)

(73) Assignee: Abbott Biotechnology Ltd., Hamilton (BM)

( * ) Notice: Subject to any disclaimer, the term of this patent is extended or adjusted under 35 U.S.C. 154(b) by 280 days.

(21) Appl. No.: 11/591,241

(22) Filed: Oct. 31, 2006

(65) Prior Publication Data

US 2007/0172897 A1 Jul. 26, 2007

Related U.S. Application Data

(60) Provisional application No. 60/732,444, filed on Nov. 1, 2005.

(51) Int. Cl.
*C12Q 1/00* (2006.01)
*C12Q 1/37* (2006.01)
*G01N 33/573* (2006.01)
*G01N 33/68* (2006.01)

(52) U.S. Cl. ........... 435/7.21; 435/4; 435/7.4; 435/7.92; 435/23; 436/86

(58) Field of Classification Search ........................ None
See application file for complete search history.

(56) References Cited

U.S. PATENT DOCUMENTS

| | | | |
|---|---|---|---|
| 5,656,272 A | 8/1997 | Le et al. | |
| 6,090,382 A * | 7/2000 | Salfeld et al. | 424/133.1 |
| 6,153,732 A * | 11/2000 | Eyre | 530/387.9 |
| 6,258,562 B1 * | 7/2001 | Salfeld et al. | 435/69.6 |
| 6,448,380 B2 | 9/2002 | Rathjen | |
| 6,451,983 B2 | 9/2002 | Rathjen | |
| 6,498,237 B2 | 12/2002 | Rathjen | |
| 6,506,607 B1 | 1/2003 | Shyjan | |
| 6,509,015 B1 | 1/2003 | Salfeld et al. | |
| 6,607,879 B1 | 8/2003 | Cocks et al. | |
| 7,070,775 B2 | 7/2006 | Le | |
| 7,192,584 B2 | 3/2007 | Le | |
| 7,223,394 B2 | 5/2007 | Salfeld et al. | |
| 7,250,165 B2 | 7/2007 | Heavner | |
| 7,276,239 B2 | 10/2007 | Le | |
| 7,541,031 B2 | 6/2009 | Salfeld et al. | |
| 7,588,761 B2 | 9/2009 | Salfeld et al. | |
| 2003/0012786 A1 | 1/2003 | Teoh et al. | |
| 2003/0049725 A1 | 3/2003 | Heavner | |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2003/0235585 A1 | 12/2003 | Fischkoff et al. | |
| 2004/0009172 A1 | 1/2004 | Fischkoff et al. | |
| 2004/0033228 A1 | 2/2004 | Krause et al. | |
| 2004/0120952 A1 | 6/2004 | Knight | |
| 2004/0126372 A1 * | 7/2004 | Banerjee et al. | 424/145.1 |
| 2004/0126373 A1 | 7/2004 | Banerjee et al. | |
| 2004/0131614 A1 | 7/2004 | Banerjee et al. | |
| 2004/0136989 A1 | 7/2004 | Banerjee et al. | |
| 2004/0136990 A1 | 7/2004 | Banerjee et al. | |
| 2004/0136991 A1 | 7/2004 | Banerjee et al. | |
| 2004/0151722 A1 | 8/2004 | Banerjee et al. | |
| 2004/0166111 A1 | 8/2004 | Kaymakcalan et al. | |
| 2004/0203072 A1 | 10/2004 | Sandell et al. | |
| 2004/0219142 A1 | 11/2004 | Banerjee et al. | |
| 2005/0123541 A1 | 6/2005 | Heavner | |
| 2005/0249735 A1 | 11/2005 | Le | |
| 2006/0009385 A1 | 1/2006 | Hoffman et al. | |
| 2006/0018907 A1 | 1/2006 | Le | |
| 2006/0083741 A1 | 4/2006 | Hoffman et al. | |
| 2006/0149042 A1 | 7/2006 | Konstantinov | |
| 2006/0153846 A1 | 7/2006 | Krause et al. | |
| 2006/0246073 A1 | 11/2006 | Knight | |
| 2006/0269479 A1 | 11/2006 | Colton et al. | |
| 2007/0003548 A1 | 1/2007 | Heavner | |
| 2007/0041905 A1 | 2/2007 | Hoffman et al. | |
| 2007/0071747 A1 | 3/2007 | Hoffman et al. | |
| 2007/0081996 A1 | 4/2007 | Hoffman | |
| 2007/0172475 A1 | 7/2007 | Matheus | |
| 2007/0172897 A1 | 7/2007 | Maksymowych et al. | |
| 2007/0184045 A1 | 8/2007 | Doctor | |
| 2007/0196373 A1 | 8/2007 | Le | |
| 2007/0202051 A1 | 8/2007 | Schuschnig | |
| 2007/0202104 A1 | 8/2007 | Banerjee et al. | |
| 2007/0237831 A1 * | 10/2007 | Sung et al. | 424/490 |
| 2007/0269463 A1 | 11/2007 | Donavan | |
| 2007/0292442 A1 | 12/2007 | Wan et al. | |
| 2007/0298040 A1 | 12/2007 | Le | |
| 2008/0025976 A1 | 1/2008 | Le | |
| 2008/0118496 A1 | 5/2008 | Medich et al. | |
| 2008/0131374 A1 | 6/2008 | Medich et al. | |
| 2008/0166348 A1 | 7/2008 | Kupper et al. | |
| 2008/0193466 A1 | 8/2008 | Banerjee et al. | |
| 2008/0227136 A1 | 9/2008 | Pla et al. | |
| 2008/0311043 A1 | 12/2008 | Hoffman et al. | |
| 2009/0017472 A1 | 1/2009 | Stuhlmuller et al. | |
| 2009/0028794 A1 | 1/2009 | Medich et al. | |
| 2009/0110679 A1 | 4/2009 | Li et al. | |
| 2009/0123378 A1 | 5/2009 | Wong et al. | |
| 2009/0155205 A1 | 6/2009 | Salfeld et al. | |
| 2009/0226530 A1 | 9/2009 | Lassner et al. | |

(Continued)

FOREIGN PATENT DOCUMENTS

WO WO9729131 8/1997

(Continued)

OTHER PUBLICATIONS

Yang et al, Arthritis & Rheumatism, vol. 51, No. 5, 691-699, 2004.*

(Continued)

*Primary Examiner* — David A Saunders
(74) *Attorney, Agent, or Firm* — McCarter & English, LLP; Cristin Howley Cowles; Deborah L. Nagle

(57) ABSTRACT

The invention provides a method for determining the efficacy of a TNFα inhibitor, such as a TNFα antibody, or an antigen-binding portion thereof, for treating ankylosing spondylitis (AS), using a collagen degradation biomarker and/or a synovitis biomarker.

38 Claims, 4 Drawing Sheets

U.S. PATENT DOCUMENTS

| | | |
|---|---|---|
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |

FOREIGN PATENT DOCUMENTS

| | | |
|---|---|---|
| WO | WO02/12502 | 2/2002 |
| WO | WO2006040357 | 4/2006 |

OTHER PUBLICATIONS

Asli, Bouchra et al., "Inhibition of Tumor Necrosis Factor α and Ankylosing Spondyiltis," *N. Engl. J. Med.*, vol. 348(4):359-361 (2003).

Boeger, C.A. et al., "Treatment of ankylosing spondylitis with infliximab," *Ann. Rheum. Dis.*, vol. 60(12):1159-1160 (2001).

Brandt, Jan et al., "Successful Short Term Treatment of Severe Undifferentiated Spondyloarthropathy with the Anti-Tumor Necrosis Factor-α Monoclonal Antibody Infliximab," *The Journal of Rheumatology*, vol. 29(1):118-122 (2002).

Brandt, Jan et al., "Successful Treatment of Active Ankylosing Spondylitis with the Anti-tumor Necrosis Factor α Monoclonal Antibody Infliximab," *Arthritis & Rheumatism*, vol. 43(6):1346-1352 (2000).

Braun, J. et al., "Anti-TNFα: a new dimension in the pharmacotherapy of the spondyloarthropathies!?," *Ann. Rheum. Dis.*, vol. 59(6):404-407 (2000).

Braun, J. et al., "Anti-tumour necrosis factor α therapy for ankylosing spondylitis: International experience," *Ann. Rheum. Dis.*, vol. 61(Suppl. III):iii51-iii60 (2002).

Braun, J. et al., "Biologic therapies in the spondyloarthritis: new opportunities, new challenges," *Curr. Opin. Rheumatol.*, vol. 15:394-407 (2003).

Braun, J. et al., "International ASAS consensus statement for the use of anti-tumour necrosis factor agents in patients with ankylosing spondylitis," *Ann. Rheum. Dis.*, vol. 62:817-824 (2003).

Braun, Jürgen et al., "New treatment options in spondyloarthropathies: increasing evidence for significant efficacy of anti-tumor necrosis factor therapy," *Current Opinion in Rheumatology*, vol. 13:245-249 (2001).

Braun, Juergen et al., "Novel approaches in the treatment of ankylosing spondylitis and other spondyloarthritides," *Expert Opin. Investig. Drugs*, vol. 12(7):1097-1109 (2003).

Braun, J. et al., "Persistent clinical response to the anti-TNF-α antibody infliximab in patients with ankylosing spondylitis over 3 years," *Rheumatology*, vol. 44:670-676 (2005).

Braun, Juergen et al., "Therapy of ankylosing spondylitis and other spondyloarthritides: established medical treatment, anti-TNF-α therapy and other novel approaches," *Arthritis Res.*, vol. 4:307-321 (2002).

Braun, J. et al., "Treatment of active ankylosing spondylitis with infliximab: a randomised controlled multicentre trial," *Lancet*, vol. 359:1187-1193 (2002).

Breban, M. et al., "Efficacy of infliximab in refractory ankylosing spondylitis: results of a six-month open-label study," *Rheumatology*, vol. 41:1280-1285 (2002).

Briot, K. et al., "Body weight, body composition, and bone turnover changes in patients with spondyloarthropathy receiving anti-tumour necrosis factor α treatment," *Ann. Rheum. Dis.*, vol. 64:1137-1140 (2005).

Casset, Florence et al., "A peptide mimetic of an anti-CD4 monoclonal antibody by rational design," *Biochemical and Biophysical Research Communications*, vol. 307:198-205 (2003).

Cherouvim, E.P. et al., "Infliximab Therapy for Patients With Active and Refractory Spondyloarthropathies at the Dose of 3 mg/kg," *J. Clin. Rheumatol.*, vol. 10:162-168 (2004).

Choi, Kang-Seuk et al., "Monoclonal antibody-based competitive ELISA for simultaneous detection of rinderpest virus and peste des petits ruminants virus antibodies," *Veterinary Microbiology*, vol. 96:1-16 (2003).

Davis, J.C. Jr. et al., "New therapies for ankylosing spondylitis: etanercept, thalidomide, adn pamidronate," *Rheum. Dis. Clin. North Am.*, vol. 29(3):481-494 (2003).

Dayer, Jean-Michel et al., "Anti-TNF-α Therapy for Ankylosing Spondylitis, a Specific or Nonspecific Treatment?" *N. Engl. J. Med.*, vol. 346(18):1399-1400 (2002).

De Keyser, Filip et al., "Anti-TNF-alpha therapy in ankylosing spondylitis," *Cytokine*, vol. 33:294-298 (2006).

den Broeder, A.A. et al., "Long term anti-tumour necrosis factor α monotherapy in rheumatoid arthritis: effect on radiological course and prognostic value of markers of cartilage turnover and endothelial activation," *Ann. Rheum. Dis.*, vol. 61:311-318 (2002).

Dernis, E. et al., "Infliximab in spondylarthropathy—Influence on bone density," *Clin. Exp. Rheumatol.*, vol. 20(Suppl. 28):S185-S186 (2002).

Garnero, Patrick et al., "Association of Baseline Levels of Urinary Glucosyl-Galactosyl-Pyridinoline and Type II Collagen C-Telopeptide With Progression of Joint Destruction in Patients With Early Rheumatoid Arthritis," *Arthritis & Rheumatism*, vol. 46(1):21-30 (2002).

Gorman, Jennifer D. et al., "Treatment of Ankylosing Spondylitis by Inhibition of Tumor Necrosis Factor α," *The New England Journal of Medicine*, vol. 346(18):1349-1356 (2002).

Hawley, Peter et al., "Evaluation of an ELISA Assay for the Simultaneous Detection of HIV-1 Antibodies and Hepatitis B Surface Antigen," *VII International Conference on AIDS*, Abstracts vol. II, p. 345, No. W.C.3196 (1991).

Horneff, G. et al., "TNF-α antagonists for the treatment of juvenile-onset spondyloarthritides," *Clin. Exp. Rheumatol.*, vol. 20(Suppl. 28):S137-S142 (2002).

Kaiser, M.J. et al., "Efficacy of infliximab (Remicade®) in the treatment of spondyloarthropathies. Two case reports," *Joint Bone Spine*, vol. 68:525-527 (2001).

Keyszer, G. et al., "Circulating levels of matrix metalloproteinases MMP-3 and MMP-1, tissue inhibitor of metalloproteinases 1 (TIMP-1), and MMP-1/TIMP-1 complex in rheumatoid disease. Correlation with clinical activity of rheumatoid arthritis versus other surrogate markers," *J. Rheumatol.*, vol. 26(2):251-258 (1999).

MacCallum, Robert M. et al., "Antibody-antigen Interactions: Contact Analysis and Binding Site Topography," *J. Mol. Biol.*, vol. 262:732-745 (1996).

Maini R et al., "Infliximab (chimeric anti-tumour necrosis factor alpha monoclonal antibody) versus placebo in rheumatoid arthritis patients receiving concomitant methotrexate: a randomised phase III trial," *The Lancet*, vol. 354:1932-39 (1999).

Maksymowych, Walter P. et al., "Canadian Rheumatology Association Consensus on the Use of Anti-Tumor Necrosis Factor-α Directed Therapies in the Treatment of Spondyloarthritis," *The Journal of Rheumatology*, vol. 30(6):1356-1363 (2003).

Maksymowych, Walter P. et al., "Etanercept Exerts Beneficial Effects on Articular Cartilage Biomarkers of Degradation and Turnover in Patients with Ankylosing Spondylitis," *J. Rheumatol.*, vol. 32:1911-1917 (2005).

Maksymowych, Walter P. et al., "Infliximab in Ankylosing Spondylitis: A Prospective Observational Inception Cohort Analysis of Efficacy and Safety," *J. Rheumatol.*, vol. 29:959-965 (2002).

Marzo-Ortega, Helena et al., "Inhibition of Tumor Necrosis Factor α and Ankylosing Spondylitis," *The New England Journal of Medicine*, vol. 348(4):359-360; author reply 360-361 (2003).

Ogilvie, A.L.J. et al., "Treatment of psoriatic arthritis with antitumor necrosis factor-α antibody clears skin lesions of psoriasis resistant to treatment with mexotrexate," *British Journal of Dermatology*, vol. 144:587-589 (2001).

Paul, William E., Fundamental Immunology, Third Edition, pp. 242, 292-295 (1993).

Pham, T. et al., "Initiation of biological agents in patients with ankylosing spondylitis: results of a Delphi study by the ASAS Group," *Ann. Rheum. Dis.*, vol. 62:812-816 (2003).

Reimold, Andreas M., "New Indications for Treatment of Chronic Inflammation by TNF-α Blockade," *The American Journal of the Medical Sciences*, vol. 325(2):75-92 (2003).

Ribbens, C. et al., "Increased matrix metalloproteinase-3 serum levels in rheumatic diseases: relationship with synovitis and steroid treatment," *Ann. Rheum. Dis.*, vol. 61:161-166 (2002).

Rudikoff, Stuart et al., "Single amino acid substitution altering antigen-binding specificity," *Proc. Natl. Acad. Sci. USA*, vol. 79:1979-1983 (1982).

Schnarr, S. et al., "Anti-tumour necrosis factor (TNF)-α therapy in undifferentiated sponsyloarthropathy," *Clin. Res. Rheumatol.*, vol. 20(Suppl. 28):S126-S129 (2002).

Sieper, J. et al., "New treatment options in ankylosing spondylitis: a role for anti-TNFα therapy," *Ann. Rheum. Dis.*, vol. 60:iii58-iii61 (2001).

Smith, David Lloyd et al., "Ibuprofen in psoriatic arthritis," *Arthritis Rheum.*, vol. 23(8):961-962 (2005).

Stokes, David G. et al., "Potential of Tumor Necrosis Factor Neutralization Strategies in Rheumatologic Disorders Other Than Rheumatoid Arthritis," *Semin. Arthritis Rheum.*, vol. 33:1-18 (2003).

Stone, Millicent et al., "Clinical and Imaging Correlates of Response to Treatment with Infliximab in Patients with Ankylosing Spondylitis," *J. Rheumatol.*, vol. 28:1605-1614 (2001).

Van den Bosch, Filip et al., "Crohn's disease associated with spondyloarthropathy: effect of TNF-α blockade with infliximab on articular symptoms," *The Lancet*, vol. 356:1821-1822 (2000).

Zou, J.X. et al., "Immunological basis for the use of TNFα-blocking agents in ankylosing spondylitis and immunological changes during treatment," *Clin. Exp. Rheumatol.*, vol. 20(Suppl. 28):S34-S37 (2002).

European Search Report for Application No. 06849865.8, dated Oct. 29, 2008.

International Search Report for Application No. PCT/US06/42564, dated Nov. 14, 2008.

International Search Report for Application No. PCT/US08/06912, dated Nov. 13, 2008.

Kim, Tae-Hwan et al., "Cartilage Biomarkers in Ankylosing Spondylitis," *Arthritis & Rheumatism*, vol. 52:885-891 (2005).

Na, Kyoung-Sun et al., "Biomarkers in Spondyloarthritis," *Current Rheumatology Reports*, vol. 8:283-286 (2006).

Poole, A. Robin, "Biologic Markers and Disc Degeneration," *The Journal of Bone & Joint Surgery*, vol. 88:72-75 (2006).

Birmingham, James D., et al., "Collagen Biomarkers for Arthritis Applications", *Biomarker Insights*, vol. 2:61-76 (2006).

Christgau, S., et al., "Collagen Type II C-telopeptide Fragments as an Index of Cartilage Degradation", *Bone*, vol. 29:209-215 (2001).

Catrina, A.I.., et al., "Anti-tumor necrosis factor (TNF)-α therapy (etanercept) down-regulates serum matrix metalloproteinase (MMP)-3 and MMP-1 in rheumatoid arthritis", *Rheumatology*, vol. 41:484-489 (2002).

Garnero, P., et al., "Cross-sectional evaluation of biochemical markers of bone, cartilage, and synovial tissue metabolism in patients with knee osteoarthritis: relations with disease activity and joint damage", *Ann Rheum Dis*, vol. 60:619-626 (2001).

Anderson J., "Ankylosing Spondylitis Assessment Group Preliminary Definition of Short-Term Improvement in Ankylosing Spondylitis," *Arthritis Rheum*. Aug. 2001; 44(8):1876-1886.

Davis, "Major Clinical Response and Partial Response in Ankylosing Spondylitis Subjects Treated with Adalimumab: The ATLAS Trial," *Arthritis Rheum*. 2005 52(9):S208-9. Poster Presentation 483 at the 2005 Annual Scientific Meeting of the American College of Rheumatology, Nov. 12-17, 2005, San Diego, California.

Davis, J. et al., "Adalimumab Reduces Pain and Fatigue in Ankylosing Spondylitis (AS) Patients—Results from the Atlas Trial," Presentation at the European League Against Rheumatism (EULAR conference, Amsterdam, The Netherlands Jun. 21-24, 2006.

Gonzalez, "High CTX-II Levels in Patients with Early Spondyloarthritis," *Gruves study (Venezuela Group for the stuffy of Spondyloarthritis) National Center for Rheumatic Diseases*, 1:1-5 (2005).

Haibel H. et al., "Adalimumab in the Treatment of Active Ankylosing Spondylitis: Results of an Open-Label, 52-Week Trial," *Ann Rheum Dis* 2005; 64(Suppl III): 316 (Poster FRI0200).

Rudwaleit, M. et al., "How to diagnose axial spondyloarthritis early," *Ann. Rheum. Dis.* 2004; 63:535-543.

van der Heijde DMFM, "Adalimumab Therapy Results in Significant Reduction of Signs and Symptoms in Subjects with Ankylosing Spondylitis: The ATLAS Trial," 2005 Arthritis Rheum; 52(9)(Suppl): S281. Oral Presentation of Abstract 691 at the 2005 Annual Scientific Meeting of the American College of Rheumatology, Nov. 12-17, 2005, San Diego, California.

Vandooren, "Involvement of Matrix Metalloproteinases and Their Inhibitors in Peripheral Synovitis and Down-Regulation by Tumor-Necrosis Factor α Blockade in Spondylarthropathy," *Arthritis & Rheumatism*, vol. 50(9): 2942-2953 (2004).

Lorenz, H., "Technology evaluation: Adalimumab, Abbott Laboratories, "*Molecular Therapeutics* 2002; 4(2):185-190.

\* cited by examiner

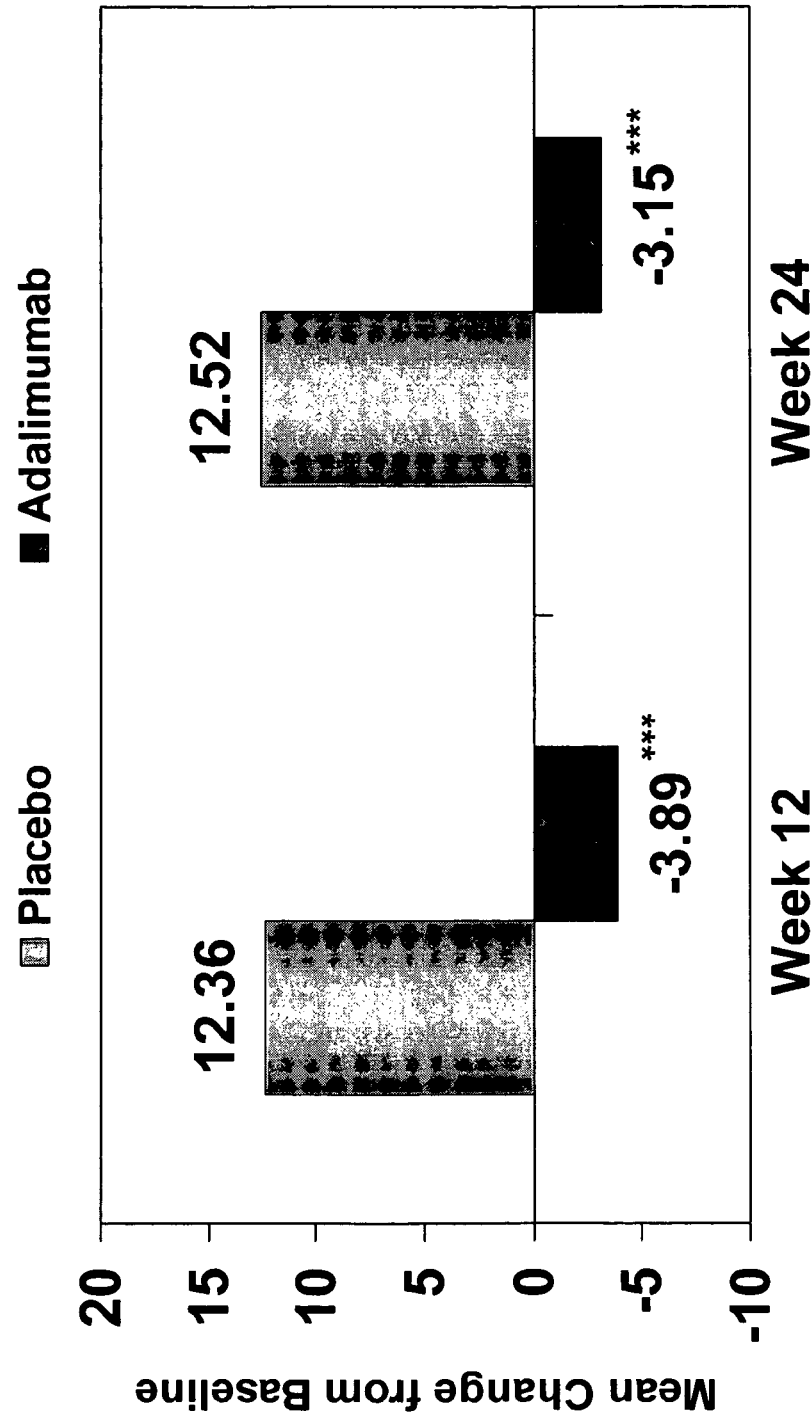

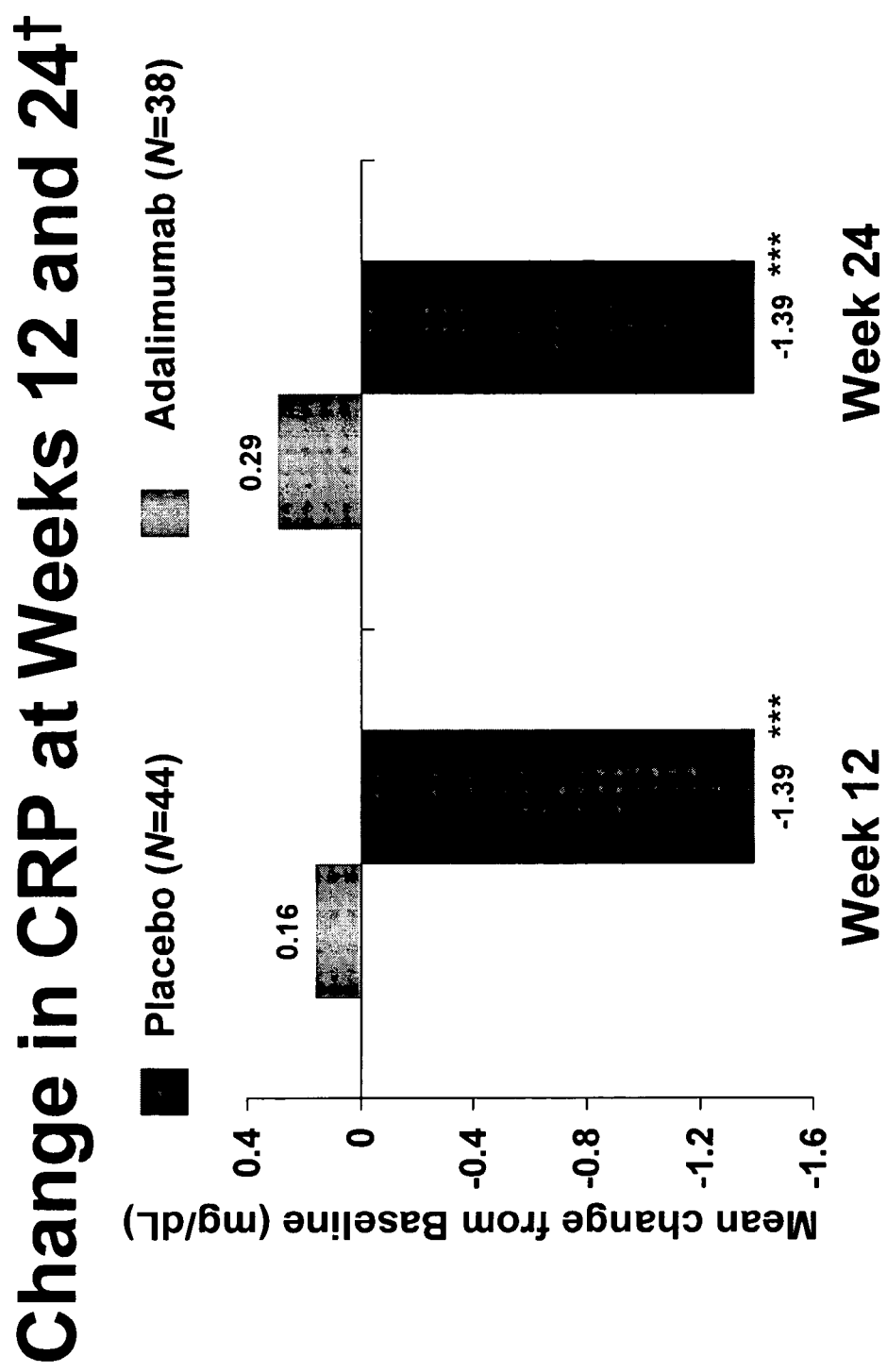

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: D2E7 heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: D2E7 light chain variable region CDR3
<220> FEATURE:
<221> NAME/KEY: VARIANT
<222> LOCATION: (9)
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
```

```
<220> FEATURE:
<221> NAME/KEY: VARIANT
<222> LOCATION: (12)
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30
```

```
Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Asp Trp Val
            35                  40                  45

Ser Ala Ile Thr Trp Asn Ser Gly His Ile Asp Tyr Ala Asp Ser Val
 50                  55                  60

Glu Gly Arg Phe Ala Val Ser Arg Asp Asn Ala Lys Asn Ala Leu Tyr
 65                  70                  75                  80

Leu Gln Met Asn Ser Leu Arg Pro Glu Asp Thr Ala Val Tyr Tyr Cys
                 85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
```

```
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3
```

```
<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLL0H1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLL0H10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25
```

```
Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
```

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial Sequence
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321

<210> SEQ ID NO 37
<211> LENGTH: 363
<212> TYPE: DNA

<213> ORGANISM: Artificial Sequence
<220> FEATURE:
<223> OTHER INFORMATION: D2E7 heavy chain variable region

<400> SEQUENCE: 37

```
gaggtgcagc tggtggagtc tggggaggc ttggtacagc ccggcaggtc cctgagactc        60
tcctgtgcgg cctctggatt cacctttgat gattatgcca tgcactgggt ccggcaagct       120
ccagggaagg gcctggaatg ggtctcagct atcacttgga atagtggtca catagactat       180
gcggactctg tggagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                     363
```

METHODS AND COMPOSITIONS FOR DETERMINING THE EFFICACY OF A TREATMENT FOR ANKYLOSING SPONDYLITIS USING BIOMARKERS

RELATED APPLICATIONS

This application claims priority to U.S. Provisional Patent Appln. 60/732,444, filed on Nov. 1, 2005, the contents of which are hereby incorporated herein by reference.

This application is related to U.S. Pat. Nos. 6,090,382, 6,258,562, and 6,509,015, each of which are incorporated by reference herein. This application is also related to U.S. patent application Ser. No. 09/801,185, filed Mar. 7, 2001; U.S. patent application Ser. No. 10/302,356, filed Nov. 22, 2002; U.S. patent application Ser. No. 10/163,657, filed Jun. 5, 2002; and U.S. patent application Ser. No. 10/133,715, filed Apr. 26, 2002; U.S. patent application Ser. No. 10/222,140, filed Aug. 16, 2002; U.S. patent application Ser. No. 10/693,233, filed Oct. 24, 2003; U.S. patent application Ser. No. 10/622,932, filed Jul. 18, 2003; U.S. patent application Ser. No. 10/623,039, filed Jul. 18, 2003; U.S. patent application Ser. No. 10/623,076, filed Jul. 18, 2003; U.S. patent application Ser. No. 10/623,065, filed Jul. 18, 2003; U.S. patent application Ser. No. 10/622,928, filed Jul. 18, 2003; U.S. patent application Ser. No. 10/623,075, filed Jul. 18, 2003; U.S. patent application Ser. No. 10/623,035, filed Jul. 18, 2003; U.S. patent application Ser. No. 10/622,683, filed Jul. 18, 2003; U.S. patent application Ser. No. 10/622,205, filed Jul. 18, 2003; U.S. patent application Ser. No. 10/622,210, filed Jul. 18, 2003; and U.S. patent application Ser. No. 10/623,318, filed Jul. 18, 2003. This application is also related to U.S. application Ser. No. 11/104,117. The entire contents of each of these patents and patent applications are hereby incorporated herein by reference.

BACKGROUND OF THE INVENTION

Elevated levels of TNF play an important role in pathologic inflammation. TNF also referred to as (TNFα) has been implicated in the pathophysiology of a variety of human diseases and disorders, including sepsis, infections, autoimmune diseases, transplant rejection and graft-versus-host disease (see e.g., Moeller et al. (1990) *Cytokine* 2:162; U.S. Pat. No. 5,231,024 to Moeller et al.; European Patent Publication No. 260 610 B1 by Moeller, A. et al.; Vasilli (1992) *Annu. Rev. Immunol.* 10:411; Tracey and Cerami (1994) *Annu. Rev. Med.* 45:491).

Ankylosing spondylitis (AS) which has been associated with elevated levels of TNF (Lange et al. (2000) *Eur J Med Res.* 5(12):507), and is a common inflammatory rheumatic disease that produces progressive spinal stiffness and restriction of mobility. AS is a form of chronic inflammation of the spine and the sacroiliac joints, which can cause pain and stiffness in and around the spine. Over time, chronic spinal inflammation (spondylitis) can lead to a complete cementing together (fusion) of the vertebrae, a process referred to as ankylosis, which, in turn, can lead to loss of mobility of the spine AS is often diagnosed using a combination of methods, including examining symptoms, physical examination, and x-ray analysis. An AS patient's symptoms may include pain and morning stiffness of the spine and sacral areas with or without accompanying inflammation in other joints, tendons, and organs. Early symptoms of AS can be very deceptive, however, as stiffness and pain in the low back can be seen in many other conditions, and, as a result, time may pass before the diagnosis of AS is even considered. In addition, physical examination of the patient may reveal signs of inflammation and decreased range of motion of joints, often particularly apparent in the spine. Flexibility of the low back and/or neck may be decreased. Further clues to the diagnosis may be suggested by x-ray abnormalities of the spine, or the presence of the blood test genetic marker, the HLA-B27 gene.

Structural damage is associated with AS, and results from degradation and resorption in cartilage and bone of the joint, resulting in joint destruction. Therapeutically, it is important to address both the symptoms of the patient having AS, as well as the structural damage caused by joint destruction associated with the disease.

Traditional treatment of AS has included administering nonsteroidal antiinflammatory drugs (NSAIDs) to the patient to decrease pain and stiffness of the spine and other joints. Commonly used NSAIDs include indomethacin (Indocin), tolmetin (Tolectin), sulindac (Clinoril), naproxen (Naprosyn), and diclofenac (Voltaren). More recently, anti-TNF biologic agents, such as etanercept, infliximab, and adalimumab, have been shown to be effective at reducing symptoms associated with AS.

SUMMARY OF THE INVENTION

Despite improvements in the treatment of AS using anti-TNF biologic agents, diagnostic and prognostic tests are needed to assist practicing physicians in diagnosing symptoms of the patient and recommending appropriate treatment regimens. In addition, diagnostic and prognostic tests are needed to better assess improvements in the patient's disease status, which can provide better medical care for the patient as well as reduced cost in treatment.

The invention provides biomarkers which may be used to determine improvements in the patients overall AS disease status, particularly with respect to structural damage associated with AS. The present invention describes a method for determining the efficacy of a TNF inhibitor for decreasing cartilage degradation and/or synovitis which is related to AS. The invention also includes a method for identifying AS patients who are candidates for treatment with TNF inhibitors, e.g., adalimumab, based on their level of cartilage degradation and/or synovitis biomarkers.

The invention describes a method for determining the efficacy of a human TNFα antibody, or an antigen-binding portion thereof, for treating ankylosing spondylitis (AS), said method comprising comparing a pre-determined level of a collagen degradation biomarker and/or a synovitis biomarker from a patient having AS following treatment with the human TNFα antibody, with a known standard level of the collagen degradation biomarker and/or the synovitis biomarker associated with the disease state; and assessing whether the patient's post-treatment collagen degradation biomarker and/or synovitis biomarker level is lower than the known standard level of the collagen degradation biomarker and/or synovitis biomarker, wherein a lower collagen degradation biomarker and/or synovitis biomarker level from the patient following treatment with the human TNFα antibody relative to the known standard level indicates efficacy of the human TNFα antibody for the treatment of AS.

The invention also provides a method of monitoring the efficacy of a human TNFα antibody, or an antigen-binding portion thereof, for decreasing the progression of structural damage associated with ankylosing spondylitis (AS) in a patient, the method comprising determining the level of a collagen degradation biomarker and/or a synovitis biomarker in a patient and comparing the level of the collagen degradation biomarker and/or a synovitis biomarker with a known standard level of the collagen degradation biomarker and/or a synovitis biomarker associated with AS, wherein a decrease in the level of the biomarker indicates that the human TNFα antibody, or an antigen-binding portion thereof, is efficacious for decreasing the rate of progression of structural damage associated with AS in the patient.

The invention includes a method for predicting the efficacy of a human TNFα antibody, or an antigen-binding portion thereof, for the treatment of AS in a patient, said method comprising comparing a pre-determined level of a collagen degradation biomarker and/or a synovitis biomarker from the patient following treatment with the human TNFα antibody, or an antigen-binding portion thereof, with a known standard level of the collagen degradation biomarker and/or a synovitis biomarker associated with AS; and assessing whether the patient's post-treatment collagen degradation biomarker and/or a synovitis biomarker level is lower than the known standard level of the collagen degradation biomarker and/or a synovitis biomarker, wherein a lower collagen degradation biomarker and/or a synovitis biomarker level from the patient relative to the known standard level indicates that the human TNFα antibody, or an antigen-binding portion thereof, is predicted to be effective for the treatment of AS in the patient.

The invention also describes a method for determining the efficacy of a human TNFα antibody, or an antigen-binding portion thereof, for ankylosing spondylitis (AS) comprising comparing a pre-treatment level of a collagen degradation biomarker and/or a synovitis biomarker obtained from a patient having AS with a post-treatment level of the collagen degradation biomarker and/or the synovitis biomarker obtained from said patient, wherein a lower post-treatment biomarker level indicates efficacy of the human TNFα antibody, or an antigen-binding portion thereof.

In one embodiment, the collagen degradation biomarker is type II collagen C-telopeptide (CTX-II). In another embodiment, the collagen degradation biomarker is urinary type II collagen C-telopeptide (CTX-II).

In one embodiment, the synovitis biomarker is matrix metalloprotease 3 (MMP3). In another embodiment, the synovitis biomarker is serum metalloprotease 3 (MMP3).

In one embodiment, the efficacy of the human TNFα antibody, or an antigen-binding portion thereof, for improving structural damage associated with AS is determined.

In one embodiment, the method of the invention further comprises comparing the patient's C-reactive protein (CRP) level with a known standard CRP level associated with the disease state; and assessing whether the patient's CRP level is higher than the known standard CRP level, wherein a lower C-reactive protein level relative to the known standard indicates efficacy of treatment.

In one embodiment, the human TNFα antibody, or antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

In one embodiment, the human TNFα antibody, or antigen-binding portion thereof, has the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In another embodiment, the human TNFα antibody, or antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

In yet another embodiment of the invention, the human TNFα antibody, or antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

In still another embodiment, the human TNFα antibody, or antigen-binding portion thereof, is adalimumab.

In yet another embodiment of the invention, the level of the biomarker is determined using ELISA.

The invention also includes a kit for performing any of the above-mentioned methods comprising a detectable agent that specifically recognizes the collagen degradation biomarker and/or a synovitis biomarker; instructions for use; and optionally, reagents for isolating a sample from the patient.

In one embodiment, the detectable agent recognizes either urinary CTX-II or serum MMP3.

The invention also provides a method of determining the efficacy of a TNFα inhibitor for the treatment of AS in a patient, said method comprising comparing a pre-determined level of CTX-II from the patient following treatment with the TNFα inhibitor with a known standard level of CTX-II associated with the disease state; and assessing whether the patient's post-treatment CTX-II level is lower than the known standard level of CTX-II, wherein a lower CTX-II level from the patient relative to the known standard level indicates that the TNFα inhibitor is effective for the treatment of AS in the patient.

The invention further provides a method for determining the efficacy of a TNFα inhibitor for decreasing structural damage associated with ankylosing spondylitis (AS) in a patient, said method comprising comparing a pre-determined level of CTX-II from the patient having AS following treatment with the TNFα inhibitor with a known standard level of CTX-II associated with the disease state; and assessing whether the patient's post-treatment CTX-II level is lower than the known standard level of CTX-II, wherein a lower CTX-II level from the patient following treatment with the TNFα inhibitor relative to the known standard level indicates that the TNFα inhibitor is effective at decreasing structural damage associated with AS in the patient.

The invention also provides a method of determining the efficacy of a TNFα inhibitor for the treatment of AS in a patient, said method comprising comparing a pre-determined, post-treatment level of CTX-II obtained from the patient with a pre-determined, pre-treatment level of CTX-II obtained from the patient; and assessing whether the post-treatment CTX-II level is lower than the pre-treatment CTX-II level, wherein a lower post-treatment CTX-II level from the patient relative to the pre-treatment CTX-II level indicates that the TNFα inhibitor is effective for the treatment of AS in the patient.

In one embodiment, the post-treatment CTX-II level is at least about a 5-10% decrease relative to the pre-treatment CTX-II level. In another embodiment, the post-treatment CTX-II level is at least about a 9% decrease relative to the pre-treatment CTX-II level. In another embodiment, the post-treatment CTX-II level is at least about 5-100%, about 5-80%, about 5-60%, about 5-45%, about 5-40%, about 5-35%, about 5-30%, about 5-25%, about 5-20%, about 5-15%, about 5-10%, about 6-9%, about 7-8%, or about 9% relative to the baseline or known standard level.

In one embodiment, the post-treatment MMP-3 level is at least about 5-50%, about 5-45%, about 5-40%, about 5-35%, about 5-30%, about 5-25%, about 5-20%, about 5-15%, about 5-13%, about 6-12%, about 7-11%, or about 8% relative to baseline or known standard level for a subject having AS. In a further embodiment, efficacy of the TNF inhibitor is shown when MMP-3 levels decrease at least about 12% relative to baseline or known standard level for a subject having AS.

In one embodiment, the CTX-II is urinary CTX-II. In one embodiment, the MMP-3 is serum MMP-3.

In one embodiment, the CTX-II level or the MMP-3 level is determined using ELISA.

The invention also describes a method of determining whether a patient having AS is a candidate for treatment with adalimumab, comprising comparing said patient's collagen degradation biomarker level with an known standard collagen degradation biomarker level from an unaffected subject, and assessing whether the patient's collagen degradation biomarker level is higher relative to the known standard collagen degradation biomarker level, wherein a higher biomarker level indicates said patient is a candidate for treatment with adalimumab.

In one embodiment, the collagen degradation biomarker is type II collagen C-telopeptide. In one embodiment, the level of the collagen degradation biomarker is determined by measuring the concentration of type II collagen C-telopeptide in the urine of the patient.

In one embodiment, the invention further comprises comparing said patient's synovitis biomarker level with a known standard synovitis biomarker level from an unaffected subject; and assessing whether the patient's synovitis biomarker level is higher relative to the known standard synovitis biomarker level, wherein a higher patient synovitis biomarker level indicates the patient is a candidate for treatment with adalimumab.

In one embodiment, the synovitis biomarker is matrix metalloprotease 3 (MMP3).

The invention includes a method of determining whether a patient having AS is a candidate for treatment with adalimumab, comprising comparing said patient's synovitis biomarker level with an known standard synovitis biomarker level from an unaffected subject, and assessing whether the patient's synovitis biomarker level is higher relative to the known standard synovitis biomarker level, wherein a higher synovitis biomarker level indicates said patient is a candidate for treatment with adalimumab In one embodiment, the synovitis biomarker is matrix metalloprotease 3 (MMP3).

In one embodiment, the level of the synovitis biomarker is determined by measuring the serum concentration of MMP3 of the patient.

In one embodiment, the invention further comprises comparing said patient's collagen degradation biomarker level with a known standard collagen degradation biomarker level from an unaffected subject; and assessing whether the patient's collagen degradation biomarker level is higher relative to the known standard collagen degradation biomarker level, wherein a higher patient collagen degradation biomarker level indicates the patient is a candidate for treatment with adalimumab.

In one embodiment, the collagen degradation biomarker is type II collagen C-telopeptide.

The invention includes a method of monitoring efficacy of a therapeutic treatment for ankylosing spondylitis (AS) comprising determining the level of a collagen degradation biomarker and/or a synovitis biomarker in a subject, wherein a decrease or change in the level of the biomarker indicates a decrease or change in the rate of progression of structural damage in AS.

In one embodiment, the collagen degradation biomarker is urinary type II collagen C-telopeptide.

In one embodiment, the synovitis biomarker is serum matrix metalloprotease 3 (MMP3).

In one embodiment, the therapeutic treatment is administration of adalimumab.

The invention also includes a method for determining structural damage in a patient having AS comprising determining the baseline level of a collagen degradation biomarker and/or a synovitis biomarker in a patient to obtain said patient's baseline biomarker level; determining the level of the collagen degradation biomarker and/or the synovitis biomarker in said patient after a period of time to obtain said patient's post-baseline biomarker level; comparing said patient's baseline biomarker level with the post-baseline biomarker level; and assessing whether patient's post-baseline biomarker level is lower than patient's baseline biomarker level, wherein a lower post-baseline biomarker level indicates a decrease in structural damage.

The invention further includes a method for modulating a collagen degradation biomarker and/or a synovitis biomarker in a patient having AS, comprising administering adalimumab to said patient.

In one embodiment, the TNFα inhibitor is selected from the group consisting of a TNFα antibody, or an antigen-binding portion thereof, a TNF fusion protein, or a recombinant TNF binding protein.

In one embodiment, the TNF fusion protein is etanercept.

In one embodiment, the TNFα antibody, or antigen-binding portion thereof, is selected from the group consisting of a chimeric antibody; a humanized antibody, a human antibody, and a multivalent antibody.

In one embodiment, the anti-TNFα antibody, or antigen-binding portion thereof, is selected from the group consisting of infliximab, golimumab, and adalimumab.

In one embodiment, the human antibody, or antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less.

In one embodiment, the human antibody, or antigen-binding portion thereof, has the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the human antibody, or antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2

In one embodiment, the invention further comprises comparing a pre-determined, post-treatment level of a synovitis biomarker obtained from the patient with a known standard level of the synovitis biomarker associated with AS; and assessing whether the post-treatment synovitis biomarker level is lower than the known standard synovitis biomarker level, wherein a lower post-treatment synovitis biomarker relative to the known standard synovitis biomarker level indicates that the TNFα inhibitor is effective for the treatment of AS in the patient.

In one embodiment, the synovitis biomarker is MMP-3.

The invention also describes a kit for performing the methods as described above, wherein the kit comprises a detectable agent that specifically recognizes CTX-II; instructions for use; and optionally, reagents for isolating a sample from the patient. In one embodiment, the kit further comprises a detectable agent that specifically recognizes MMP-3.

BRIEF DESCRIPTION OF THE FIGURES

FIG. 3 shows a graph which indicates that adalimumab patients experienced statistically significant reductions in MMP3 levels versus placebo patients at 12 weeks and 24 weeks.

FIG. 4 shows a graph which indicates that CRP levels were significantly reduced in adalimumab patients compared to placebo patients at week 12 and week 24.

DETAILED DESCRIPTION OF THE INVENTION

I. Definitions

Figure 1:
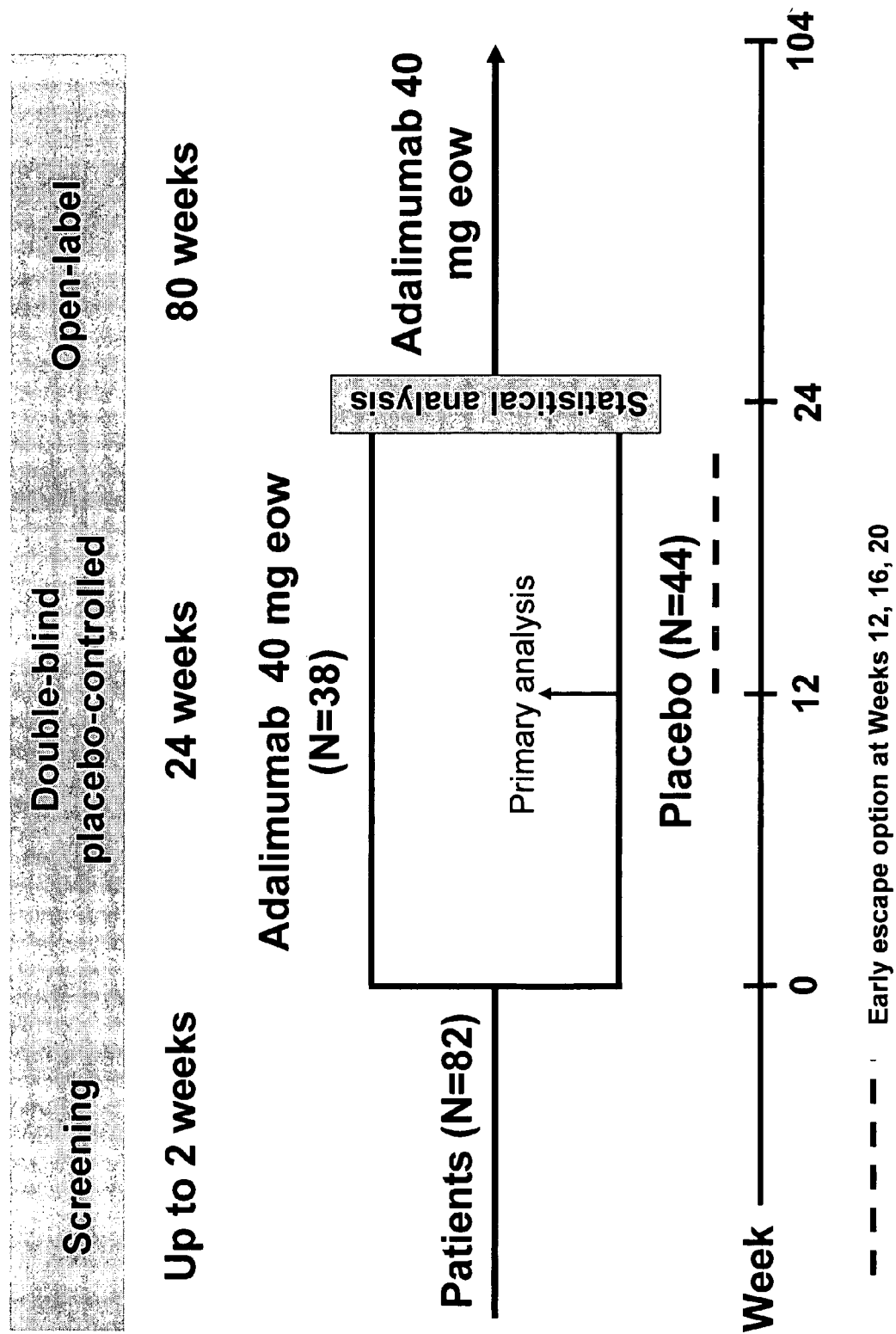
FIG. 1 shows the study design of the study described in Example 1.

In order that the present invention may be more readily understood, certain terms are first defined.

The term "biomarker", as used herein, refers generally to a molecule, i.e., a gene (or nucleic acid encoding said gene), protein, carbohydrate structure or glycolipid, the expression of which in or on a sample derived from a mammalian tissue or cell can be detected by standard methods in the art (as well as those disclosed herein), and is predictive or denotes a condition of the subject from which it was obtained. Where the biomarker is a protein, modulation or alteration of expression encompasses modulation through different post translational modifications. A biomarker may be used to distinguish disease activity, including improvements in the condition and deterioration of the condition, based on the level of the biomarker. Accordingly, in one embodiment, a biomarker useful in the present invention, is any molecule the expression of which is regulated (up or down) in a patient with a disease condition, e.g., a spondyloarthropathy, when compared to a normal control, i.e., an unaffected subject. In one embodiment, selected sets of one, two, three, and more of the biomarkers of this invention can be used as end-points for rapid diagnostics or prognostics for determining a patient's response to an anti-TNF therapy.

The term "collagen degradation biomarker" refers to a molecule, i.e., a gene (or nucleic acid encoding said gene), protein, carbohydrate structure or glycolipid, which is associated with the destruction of collagen. A collagen degradation biomarker is used to distinguish the disease activity, i.e., collagen destruction, in a subject from whom the sample or tissue is obtained. In one embodiment, the collagen degradation biomarker is a fragment of collagen, e.g., a fragment of type II collagen. In one embodiment, the collagen degradation biomarker is type II collagen C-telopeptide (CTX-II).

The term "synovitis biomarker" refers to a molecule, i.e., a gene (or nucleic acid encoding said gene), protein, carbohydrate structure or glycolipid, which is associated with synovitis, or inflammation of the synovium. A synovitis biomarker may be used to indicate an increase in turn-over, proliferation, degradation, inflammation, destruction, decomposition, pathological remodelling or degradation of the synovia or synovial collagen of a patient. In one embodiment, a synovitis biomarker is an endopeptidase associated with extra-cellular matrix (ECM) degradation, e.g., matrix metalloproteinases. In one embodiment, the synovitis biomarker used in the invention is MMP-3.

The term "known standard level" or "control level" refers to an accepted or pre-determined level of the biomarker which is used to compare the biomarker level derived from a sample of a patient. In one embodiment, the known standard level of the collagen degradation biomarker and/or the synovitis biomarker is based on a subject or subjects having AS, and, therefore, represents the disease state. In another embodiment, the known standard level of the biomarker indicates an unaffected, i.e., non-disease, state of a subject who does not have AS.

When compared to the known standard level of a certain biomarker, deviation from the known standard level generally indicates either an improvement or deterioration in the disease state. Alternatively, when compared to the known standard level of a certain biomarker, equivalence to the known standard level generally indicates confirmation of the disease activity, confirmation of a non-disease state, or, if the biomarker level of the patient is obtained following therapeutic treatment for the disease, failure of a therapy to improve a patient's disease state.

As used herein, the term "expression", when used in connection with detecting the expression of a biomarker of the present invention, can refer to detecting transcription of the gene encoding a biomarker protein, to detecting translation of the biomarker protein, and/or detecting the biomarker protein which results from metabolism of a larger protein, e.g., degradation of type II collagen which yields the CTX-II fragment. To detect expression of a biomarker refers to the act of actively determining whether a biomarker is expressed or not. To quantitate expression refers to the act of determining the level of the given biomarker, e.g., ng/ml. Detecting and/or quantitating expression can include determining whether the biomarker expression is upregulated as compared to a known standard level, downregulated as compared to a known standard level, or substantially unchanged as compared to a known standard level. Therefore, the step of quantitating and/or detecting expression does not require that expression of the biomarker actually is upregulated or downregulated, but rather, can also include detecting no expression of the biomarker or detecting that the expression of the biomarker has not changed or is not different (i.e., detecting no significant expression of the biomarker or no significant change in expression of the biomarker as compared to a control).

The term "level" or "amount" as used herein refers to the measurable quantity of a biomarker. The amount may be either (a) an absolute amount as measured in molecules, moles or weight per unit volume or cells or (b) a relative amount, e.g., measured by densitometric analysis. In a preferred embodiment levels of RNA and/or protein of the biomarker are determined.

The term "subject" or "patient," as used herein, refers to either a human or non-human animal.

The term "sample" as used herein refers to a collection of similar cells or tissue obtained from a subject. The source of the tissue or cell sample may be solid tissue as from a fresh, frozen and/or preserved organ or tissue sample or biopsy or aspirate; blood or any blood constituents; or bodily fluids, such as blood, serum, plasma, urine, saliva, sweat or synovial fluid. In one embodiment, the synovitis biomarker is obtained from a serum sample. In one embodiment, the cartilage degradation biomarker is obtained from a urine sample.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immmunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173, 494; PCT International Publication No. WO 86/01533; U.S. Pat. No. 4,816,567; European Patent Application No. 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060, Queen et al., *Proc. Natl. Acad. Sci. USA* 86:10029-10033 (1989); U.S. Pat. No. 5,530,101, U.S. Pat. No. 5,585,089, U.S. Pat. No. 5,693,761, U.S. Pat. No. 5,693, 762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382).

Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "dose," as used herein, refers to an amount of TNFα inhibitor which is administered to a subject.

The term "multiple-variable dose" includes different doses of a TNFα inhibitor which are administered to a subject for therapeutic treatment. "Multiple-variable dose regimen" or "multiple-variable dose therapy" describe a treatment schedule which is based on administering different amounts of TNFα inhibitor at various time points throughout the course of treatment. Multiple-variable dose regimens are described in PCT application no. PCT/US05/12007.

The term "dosing", as used herein, refers to the administration of a substance (e.g., an anti-TNFα antibody) to achieve a therapeutic objective (e.g., the treatment of rheumatoid arthritis).

The terms "biweekly dosing regimen", "biweekly dosing", and "biweekly administration", as used herein, refer to the time course of administering a substance (e.g., an anti-TNFα antibody) to a subject to achieve a therapeutic objective. The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "kit" as used herein refers to a packaged product comprising components with which to administer the TNFα antibody of the invention for treatment of a TNFα-related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody D2E7, as described in PCT/IB03/04502 and U.S. application Ser. No. 10/222,140.

Various aspects of the invention are described in further detail herein.

II. Cartilage Degradation and Spondylitis Biomarkers

There exists a need to establish a meaningful assessment tool for ankylosing spondylitis (AS) to be able to determine improvements, especially early structural improvements, in AS patients undergoing TNF inhibitor therapy. Currently, erythrocyte sedimentation rate (ESR) and the level of C-reactive protein (CRP) are the most widely used methods for assessing AS activity, however these markers alone are insufficient for evaluating AS disease activity (Ruof and Stucki (1999) *J Rheumatol* 26:966). The invention provides biomarkers which have been identified as being useful in assessing the ability of an anti-TNF therapy to prevent structural damage associated with AS in a patient. In addition, the invention provides a method for determining a patient's response to improvements in structural destruction of joints associated with AS. The methods described herein identify changes in the progression of structural damage in a patient which might not be readily apparent using more traditional means, such as radiography. The methods of the invention are advantageous, as they provide a means for the physician to determine the efficacy of an anti-TNF treatment in a patient without having to wait for clinical outcomes, which may take prolonged periods of time.

Generally, the invention includes comparing biomarker levels from a patient having AS, or suspected of having AS, with a known standard level associated with disease activity, to determine whether the patient's biomarker level is increased, decreased, or the same, relative to the control. In determining the efficacy of a TNF inhibitor for treating AS in a patient, particularly with respect to improving structural damage, biomarker levels may be pre-determined, or, alternatively, may include obtaining a sample from the patient and then using the biomarker level determined from the sample in the comparative assessment of the invention.

The invention identifies certain biomarkers associated with structural destruction, including cartilage degradation and synovitis, which may be used to determine whether the elected anti-TNF therapy is adequate for treatment or whether a different therapy, including a different anti-TNF therapy, should be considered. Such predictive means benefit the overall health of the subject, as faster responses can be made to determine the appropriate therapy. The methods described herein also decrease the overall cost of the treatment process by more quickly eliminating ineffective therapies.

The invention provides a method for determining the efficacy of a TNF inhibitor for the treatment of a spondyloarthropathy, e.g. ankylosing spondylitis, comprising measuring biomarkers for cartilage destruction and synovitis. Efficacy is determined according to the ability of the TNF inhibitor to decrease biomarkers known to reflect disease activity relating to cartilage degradation and/or synovitis in a subject.

In one embodiment, the invention includes a method for determining the efficacy of a TNFα inhibitor, e.g., a human TNFα antibody, or an antigen-binding portion thereof, for treating ankylosing spondylitis (AS), where a pre-determined level of a collagen degradation biomarker and/or a synovitis biomarker from a patient having AS following treatment with the TNFα inhibitor (post-treatment biomarker level) is compared with a known standard level of the collagen degradation biomarker and/or the synovitis biomarker associated with the disease state. Once the two levels are compared, it is determined whether the patient's post-treatment collagen degradation biomarker and/or synovitis biomarker level is lower than the known standard level, wherein a lower collagen degradation biomarker and/or synovitis biomarker level from the patient following treatment with the TNFα inhibitor relative to the known standard level indicates efficacy of the TNFα inhibitor for the treatment of AS.

In another embodiment, the invention provides a method for determining the efficacy of a TNF inhibitor, e.g., a human TNFα antibody, or an antigen-binding portion thereof, for ankylosing spondylitis (AS) comprising comparing a pre-treatment level of a collagen degradation biomarker and/or a synovitis biomarker obtained from a patient having AS with a post-treatment level of the collagen degradation biomarker and/or the synovitis biomarker obtained from said patient, wherein a lower post-treatment biomarker level indicates efficacy of the TNF inhibitor for treating AS in the patient.

By decreasing the level of a biomarker associated with cartilage degradation and/or synovitis, a TNF inhibitor can be used to decrease or prevent structural damage associated with AS. In one aspect, the invention provides a method of monitoring the efficacy of a TNF inhibitor, e.g., a human TNFα antibody, or an antigen-binding portion thereof, for decreasing the progression of structural damage associated with ankylosing spondylitis (AS) in a patient comprising determining the level of a collagen degradation biomarker and/or a synovitis biomarker in a patient and comparing the level of the collagen degradation biomarker and/or a synovitis biomarker with a known standard level of the collagen degradation biomarker and/or a synovitis biomarker associated with AS. In this instance, a decrease in the level of the biomarker from the patient relative to the known standard level indicates that the TNF inhibitor is efficacious for decreasing the rate of progression of structural damage associated with AS in the patient.

In another aspect, the invention provides a method for predicting the efficacy of a TNF inhibitor, e.g., human TNFα antibody, or an antigen-binding portion thereof, for the treatment of AS in a patient comprising comparing a pre-determined level of a collagen degradation biomarker and/or a synovitis biomarker from the patient following treatment with the human TNFα antibody, or an antigen-binding portion thereof, with a known standard level of the collagen degradation biomarker and/or a synovitis biomarker from a patient having AS. Based on the two biomarker levels, an assessment is made regarding whether the patient's post-treatment collagen degradation biomarker and/or a synovitis biomarker level is lower than the known standard level of the collagen degradation biomarker and/or a synovitis biomarker. In this instance, a lower collagen degradation biomarker and/or a synovitis biomarker level from the patient relative to the known standard level indicates that the human TNFα antibody, or an antigen-binding portion thereof, is predicted to be effective for the treatment of AS in the patient.

In the above situations where it is determined that TNF inhibitor is effective at reducing biomarkers associated with cartilage destruction and/or synovitis, which, in turn, reflects a decrease in structural destruction, i.e., joint destruction, continuation of the TNF inhibitor treatment may be considered. In one embodiment, one may consider administering the same dosing regimen to the patient. Alternatively, one may consider reducing the dose of the TNF inhibitor shown to be effective at treating AS in the patient.

The invention provides a method of using a cartilage degradation biomarker alone or in combination with a synovitis biomarker, as well as a method of using a synovitis biomarker alone or in combination with cartilage degradation biomarker, for determining the efficacy of a TNF inhibitor treatment for AS.

In addition, analysis of collagen degradation and/or synovitis biomarker may be performed on a sample from a patient who has not yet received therapy with a TNF inhibitor. An analysis of collagen degradation and synovitis biomarkers may be performed to determine if the patient is likely to respond to treatment with an anti-TNFα antibody, e.g., adalimumab. Comparable levels of a collagen degradation and/or synovitis biomarker from a sample of a patient relative to a known standard level characterized as a level indicative of AS, may indicate that the patient has AS and, therefore, would be a candidate for treatment with a TNF inhibitor. Accordingly, such a patient may be selected for treatment with an anti-TNFα antibody, e.g., adalimumab, in order to prevent structural damage which may occur with the progression of the disease.

In one embodiment, the control level is based on the patient's own baseline level of the cartilage degradation and/or synovitis biomarker, where the baseline level is determined prior to treatment with the TNF inhibitor. In such an instance, the cartilage degradation and/or synovitis biomarker level which is determined following treatment is compared to the baseline level of the patient. Thereafter, a determination is made whether the TNF inhibitor is efficacious based on whether the cartilage degradation and/or synovitis biomarker level decreased in the patient following treatment. In another embodiment, the baseline level which is used as a control is based on the patient's own level of the cartilage degradation and/or synovitis biomarker at a given point during treatment with the TNF inhibitor, where the baseline level at the given time point during treatment is compared to a biomarker level at a given time thereafter while the patient remains on the treatment.

In one embodiment, the known standard level is based on an accepted level of the cartilage degradation and/or synovitis biomarker associated with the disease state, i.e. associated with patient(s) having AS. The known standard level of the cartilage degradation and/or synovitis biomarker level may be based on a single AS patient or, alternatively, on the average obtained from a group of AS patients. For example, in one embodiment, the known standard level of serum MMP-3 for an AS patient is between about 10-200, about 15-180, about 20-140, about 30-120, about 40-100, about 50-80, about 25-57, or about 60-70 ng/ml. In another embodiment, the known standard level of urinary CTX-II for an AS patient is between about 300-1000, about 300-800, about 300-600, about 315-395, about 320-390, about 325-385, about 330-380, about 325-385, about 324-388, about 335-375, about 340-370, about 345-365, or about 350-360 ng/ml.

Alternatively, in another embodiment, the known standard level may be based on cartilage degradation and/or synovitis biomarker levels from a healthy, unaffected subject(s). The known standard level of the cartilage degradation and/or synovitis biomarker level may be based on a single unaffected, healthy subject or, alternatively, on an average from a group of unaffected, healthy subjects. Examples of normal values of urinary CTX-II, i.e., values from healthy, non-AS subjects are described in Haima (2005) *Osteo Medical Group Clinical and Technical Monograph* and Mouritzen et al. (2003) *Annals of the Rheumatic Diseases* 62:332. For example, in one embodiment the known standard level of serum MMP-3 in an unaffected, healthy subject is between about 13 and 15 ng/ml (see Chen et al. (2006) *Rheumatology* 45:414).

Ranges intermediate to the above recited biomarker levels, e.g. about 323 to about 329 mg/ml of urinary CTX-II, are also intended to be part of this invention. In addition, ranges of values using a combination of any of the above recited values as upper and/or lower limits are intended to be included. In addition, the upper limits described above are not meant to be limiting with respect to increased levels of MMP-3 and CTX-II in patients with AS.

The level of the cartilage degradation and/or synovitis biomarker is considered altered from the control, i.e., the patient's own pre-treatment level or known standard level, if the level is either higher/increased or lower/decreased relative to the control. In one embodiment, the level of the cartilage degradation and/or synovitis biomarker derived from an AS patient is considered either higher/increased relative to the control level if the cartilage degradation and/or synovitis biomarker level is higher/increased than the control level by an amount that is greater than the standard error of the assay employed to assess the level. In one embodiment, the level of the cartilage degradation and/or synovitis biomarker derived from an AS patient is considered either lower/decreased relative to the control level if the cartilage degradation and/or synovitis biomarker level is lower/decreased than the control level by an amount that is greater than the standard error of the assay employed to assess the level. In another embodiment, the level of the cartilage degradation and/or synovitis biomarker level derived from a diseased patient can be considered higher/increased or lower/decreased than the control level if the difference in the control level and the cartilage degradation and/or synovitis biomarker level derived from a patient sample is at least about two, three, four, or five times, higher or lower than the standard error of control and sample measurements.

In one embodiment, efficacy of the TNF inhibitor is shown when CTX-II levels for a subject having AS decrease at least between about 5-100%, about 5-80%, about 5-60%, about 5-45%, about 5-40%, about 5-35%, about 5-30%, about 5-25%, about 5-20%, about 5-15%, about 5-10%, about 6-9%, about 7-8%, or about 9% relative to the baseline or known standard level. In one embodiment, efficacy of the TNF inhibitor is shown when MMP-3 levels decrease at least about 5-50%, about 5-45%, about 5-40%, about 5-35%, about 5-30%, about 5-25%, about 5-20%, about 5-15%, about 5-13%, about 6-12%, about 7-11%, or about 8% relative to baseline or known standard level for a subject having AS. In a further embodiment, efficacy of the TNF inhibitor is shown when MMP-3 levels decrease at least about 12% relative to baseline or known standard level for a subject having AS.

Ranges intermediate to the above recited biomarker levels, e.g. about 8 to about 10%, are also intended to be part of this invention. In addition, ranges of values using a combination of any of the above recited values as upper and/or lower limits are intended to be included. In addition, the upper percentage limits described above are not meant to be limiting with respect to percent decreased levels of MMP-3 and CTX-II in patients with AS, i.e., higher percent decreases are also contemplated by the invention.

Cartilage Degradation Biomarkers

Articular cartilage is composed largely of type II collagen-based fibrillar network complexed with the proteoglycan aggrecan (see Poole A R, 2003. *Rheum Dis Clin North Am* 29:803-818 and Eyre (1991) *Semin Arthritis Rheum.* 21(3 Suppl 2):2-11). In joint disease, type II collagen is progressively cleaved by collagenases. Type II collagen is degraded such that the products of the degradation process fall into three groups according to localization of the particular epitope within the collagen molecule (for review see Birmingham et al. (2006) *Biomarker Insights* 2:61, herein incorporated by reference). The different types of epitopes, including neoepitopes and telopeptide epitopes, can be used as indicators of degradative events associated with collagen.

Mature collagen type II consists of a triple helical structure with short telopeptides at both ends. The telopeptides are covalent cross-linked to other collagen strands serves to connect individual collagen molecules into a rigid fibrilar network. Fragments of mature collagen are generated when the cartilage extracellular matrix is degraded. Such fragments are found in both serum and urine and can be measured as markers for cartilage catabolism. Telopeptides include col2CTx and CTX-II (WO 91/08478; Christgau et al. (2001) *Bone* 29:209; Matyas et al. (2004) *Arthritis Rheum* 50:543; and Eyre (1989) "Peptide fragments containing HP and LP cross-links, U.S. Pat. No. 5,702,909, each of which is incorporated by reference herein).

Proteolysis causes a loss of type II collagen epitopes to body fluids, therefore, by examining type II collagen epitopes in bodily fluids, the amount of degradation of collagen can be determined (see Birmingham et al. (2006) *Biomarker Insights* 2:61 and Christgau et al. (2001) *Bone* 29:209, each of which is incorporated herein). The ability to monitor and slow or reverse the process of collagen degradation is important from a clinical standpoint, as extensive degradation of mature cross-linked type II collagen fibers is considered to be a critical, possibly even irreversible, stage in joint destruction (Billinghurst et al. (1997)).

The invention described herein uses cartilage degradation biomarkers to determine the efficacy of a TNF inhibitor for the treatment of AS, which has a disease component which includes structural damage, i.e., joint damage. In one embodiment, CTX-II, which is localized almost exclusively in cartilage, is a used in the methods and compositions of the invention as a biomarker of cartilage breakdown.

CTX-II

In a preferred embodiment, the collagen degradation biomarker is type II collagen C-telopeptide (CTX-II). CTX-II is a fragment of collagen, originating from the C-terminal type II collagen. CTX-II is identical to neoepitope Col2CTx, found at the C-terminus of the ¼ length fragment of cleaved type II collagen (for review, see Birmingham et al. (2006), incorporated by reference herein).

CTX-II is known as a biomarker for cartilage degradation. CTX-II was first associated with cartilage degradation in patients with knee osteoarthritis (Garnero et al. (2001) *Annals Rheum Dis* 60:619), wherein subsequent elevation of CTX-II in urine of patients with severe osteoarthritis was determined (Jung et al. (2004) *Pathobiol* 71:70). CTX-II has also been shown to correlate with degree of joint destruction (Christgau et al. (2001) *Bone* 29:209; Gamero and Delmas (2003) *Curr Op Rheumat* 25:641).

In one aspect, the invention provides a method of determining the efficacy of a TNFα inhibitor for the treatment of AS in a patient comprising comparing a pre-determined level of CTX-II from the patient following treatment with the TNFα inhibitor with a known standard level of CTX-II associated with AS. An assessment is then made regarding the relationship between the two levels of CTX-II to determine whether the patient's post-treatment CTX-II level is lower than the known standard level of CTX-II. A decreased level of CTX-II relative to a known standard representing the AS disease state indicates that the TNFα inhibitor is effective for the treatment of AS in the patient. In such an instance, the known standard level would represent a CTX-II level from a subject have AS disease activity, i.e., an affected, untreated patient.

In another aspect, the invention provides a method for determining the efficacy of a TNFα inhibitor for decreasing structural damage associated with ankylosing spondylitis (AS) in a patient comprising comparing a pre-determined level of CTX-II from the patient having AS following treatment with the TNFα inhibitor with a known standard level of CTX-II associated with AS. An assessment is then made regarding the two levels of CTX-II to determine whether the patient's post-treatment CTX-II level is lower than the known standard level of CTX-II. If the patient's level of CTX-II is lower CTX-II relative to the known standard level, then such a result indicates that the TNFα inhibitor is effective at decreasing structural damage associated with AS in the patient.

In one embodiment, the invention describes a method for determining the efficacy of a TNFα inhibitor for the treatment of AS in a patient comprising comparing a pre-determined, post-treatment level of CTX-II obtained from the patient with a pre-determined, pre-treatment level of CTX-II obtained from the patient. An assessment is then made regarding the two levels of CTX-II to determine whether the post-treatment CTX-II level is lower than the pre-treatment CTX-II level, wherein a lower post-treatment CTX-II level from the patient relative to the pre-treatment CTX-II level indicates that the TNFα inhibitor is effective for the treatment of AS in the patient.

Synovitis Biomarkers

Synovitis (inflammation) is now known to occur early in inflammatory diseases, such as osteoarthritis, and is associated with radiological progression of the disease. The process by which inflammation, including subclinical inflammation, may exacerbate joint damage is likely to involve changes in chondrocyte function, enhanced angiogenesis, and/or accelerated bone turnover (Bonnet and Walsh D A. (2005) *Rheumatology* 44:7-16). The invention described herein uses synovial biomarkers to determine the efficacy of a TNF inhibitor for the treatment of AS. In one embodiment, serum MMP-3, which likely originates in the inflamed joint (Kruithof et al. (2005) *Arthritis Rheum* 52:3898), is used as a synovitis biomarker to determine the efficacy of a TNF inhibitor for the treatment of AS.

MMP-3

The degradation of cartilage matrix molecules involves zinc-dependent endopeptidases, namely matrix metalloproteinases (MMPs). MMPs, a family of Zn2+-dependent endopeptidases, cleave extracellular matrix (ECM) constituents such as collagens and proteoglycans. MMPs mediate different physiological processes by digesting components of the extracellular matrix.

MMP3 is an enzyme which degrades fibronectin, laminin, collagens III, IV, IX, and X, and cartilage proteoglycans. There are currently at least 20 types of human MMPs, which are grouped according to the structure and specific substrate in: collagenase (MMP-1, -8, -13), stromelisin, gelatinase (MMP-2, -9) and plasma membrane-binding metalloproteinases (see, e.g., Nabeshima K et al. 2002 *Pathol Int* 52: 255-64).

In a preferred embodiment, the synovitis biomarker used in the invention is MMP-3. MMP-3 serum levels have been shown to be increased in inflammatory rheumatic diseases characterized by joint synovitis, such as RA, polymyalgia rheumatica, psoriatic arthritis, and acute crystal arthritis. MMP-3 serum levels are accepted as reflecting synovial inflammation (see Ribbens et al. (2002) *Annals of the Rheumatic Diseases* 61:161). In addition, previous studies have correlated matrix metalloproteinases (MMPs), specifically MMP-3 (stromelysin 1), with the Bath Ankylosing Spondylitis Disease Activity Index (BASDAI) value in AS patients (see Yang, C. et al. (2004) *Arthritis Rheum* 51:691-9).

The amino acid sequence of MMP-3 is known and can be found in, for example, GenBank Accession No. AAI07491. The nucleotide acid sequence of MMP-3 is also known and can be found in, for example, GenBank Accession No. NM002422.

The invention further includes use of the cartilage degradation biomarker, e.g., CTX-II, and the synovitis biomarker, e.g., MMP-3, either alone or in combination with one another, to achieve the methods of the invention. In addition, either biomarker may be used in combination with C-reactive protein to further determine the efficacy of the TNF inhibitor for the treatment of AS.

C-reactive protein (CRP) levels may be used in combination with a cartilage degradation biomarker, e.g., CTX-II, and the synovitis biomarker, e.g., MMP-3, as an indicator of AS disease status and the efficacy of a given anti-TNF therapy. CRP belongs to the pentraxin family of proteins, so-called because it has five identical subunits, encoded by a single gene on chromosome 1, which associate to form a stable disc-like pentameric structure. CRP is exclusively made in the liver and is secreted in increased amounts within 6 hours of an acute inflammatory stimulus. Elevated levels of CRP provide a sensitive index of ongoing inflammation, and, therefore, provides a valuable adjunct to a careful clinical assessment.

Assays to Determine Level of Biomarkers

The level of a cartilage degradation and/or synovitis biomarker in a sample can be analyzed by a number of methodologies known in the art. Once the sample is obtained from the patient, any method known in the art to be suitable for detecting and quantitating a cartilage degradation or synovitis biomarker for use in the methods of the invention may be used (either at the nucleic acid or, preferably, at the protein level). Such methods are well known in the art and include but are not limited to Western blots, Northern blots, Southern blots, immunohistochemistry, ELISA, e.g., amplified ELISA, quantitative blood based assays, e.g., serum ELISA, quantitative urine based assays, e.g., to examine levels of protein expression or degradation in the case of CTX-II, immunoprecipitation, immunofluorescence, flow cytometry, immunocytochemistry, mass spectrometrometric analyses, e.g., MALDI-TOF and SELDI-TOF, nucleic acid hybridization techniques, nucleic acid reverse transcription methods, and nucleic acid amplification methods. Examples of such assays are described in more detail below:

Protein-Based Assays

The methods of the invention may be performed using protein-based assays to determine the level of the given biomarker. Examples of protein-based assays include immunohistochemical and/or Western analysis, quantitative blood based assays, e.g., serum ELISA, and quantitative urine based assays, e.g., urine ELISA. In one embodiment, an immunoassay is performed to provide a quantitiative assessment of the given biomarker.

Proteins from patient samples can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

The amount of cartilage degradation or synovitis biomarker may be determined by detecting or quantifying the corresponding expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, and Western blotting.

In one embodiment the level of cartilage degradation or synovitis biomarker may be determined using an immunoassay. The use of antibodies directed to biomarkers described herein can be used to screen human biological samples, e.g., fluids, for the levels of the specific biomarker antigen, i.e., collagen degradation and/or synovitis biomarkers. By way of illustration, human fluids, such as blood serum or urine, can be taken from a patient and assayed for a specific epitope, either as released antigen or membrane-bound on cells in the sample fluid, using anti-biomarker antibodies in standard RIAs or ELISAs, for example, known in the art. The antibodies used in such methods are preferably monoclonal antibodies. In one embodiment, in vitro immunoserological evaluation of sera withdrawn from patients thereby permits non-invasive determination of the progression or reduction of cartilage degeneration, as well as an increase or decrease in synovitis based on sera levels of corresponding biomarkers. In one embodiment, an immunoassay for quantitative assessment of cartilage degradation measuring the CTX-II level in human urine is performed. In one embodiment, an immunoassay for quantitative assessment of synovitis measuring the MMP-3 leves in human serum is performed.

In immunoassays, the agent for detecting a cartilage degradation or synovitis biomarker polypeptide may be an antibody capable of binding to the protein of the cartilage degradation or synovitis biomarker. Antibodies can be polyclonal, or more preferably, monoclonal. An intact antibody, or a fragment thereof (e.g., Fab or $F(ab')_2$) can be used.

In one embodiment, antibodies directed to CTX-II, including urine CTX-II, are used in immunoassays, e.g., ELISA, to determine the level of CTX-II in a sample from a patient having AS. In one embodiment, CTX-II levels may be measured either in urine or serum samples from a patient. In one embodiment, an antibody which may be used in the methods and compositions of the invention for detecting and quantitating human urine CTX-II is monoclonal antibody mAbF46 (see Christgau et al. (2001) *Bone* 29:209) and F4601 (see Oestergaard et al. (2006) *Osteoarthritis Cartilage*. 14(7):670).

In one embodiment, antibodies directed to MMP-3, including serum MMP-3, are used in immunoassays, e.g., ELISA, to determine the level of MMP-3 in a sample from a patient having AS. In one embodiment, MMP-3 may be measured in serum samples from the patient. In one embodiment, an antibody for detecting and quantitating human serum MMP-3 is monoclonal antibody mAb1B4 (Murray G I et al. *Gut* 43:791-7 (1998)).

Competitive binding assays may be used to determine the level of the protein corresponding to the collagen degradation and/or synovitis biomarker. One example of a competitive binding assay is an enzyme-linked immunosorbent sandwich assay (ELISA). ELISA can be used to detect the presence of collagen degradation and/or synovitis biomarker in a sample. ELISA is a sensitive immunoassay that uses an enzyme linked to an antibody or antigen as a marker for the detection of a specific protein, especially an antigen or antibody. ELISA is an assay wherein bound antigen or antibody is detected by a linked enzyme that generally converts a colorless substrate into a colored product, or a product which can be detected. One of the most common types of ELISA is "sandwich ELISA." In one embodiment, the level of the cartilage degradation and/or synovitis biomarker is determined using an ELISA assay.

In addition, a skilled artisan can readily adapt known protein/antibody detection methods for use in determining the amount of a marker of the present invention (i.e., CTX-II and/or MMP-3).

Methods for assaying CTX-II as a biomarker for joint destruction are known in the art, and are described, for example, in Oestergaard et al. (2006) *Osteoarthritis Cartilage*. 14(7):670 and Mouritzen et al. (2003) *Annals of the Rheumatic Diseases* 62:332, incorporated by reference herein. Assays for determining levels of CTX-II are commercially available, including, for example, Urine Cartilaps® and Serum Cartilaps® (Nordic Bioscience Diagnostics). The Urine Cartilaps® assay has been used in clinical studies for quantitative assessment of cartilage degradation in rheumatoid arthritis and osteoarthritis. For example, Urine Carti-Laps® ELISA is based on the competitive binding of a monoclonal antibody to urinary fragments of type II collagen, i.e., CTX-II or to biotinylated, synthetic peptides bound to the surface of microtitre plates coated with streptavidin. Initially, biotinylated, synthetic peptides are bound to the surface of streptavidin-coated wells of the microtitre plate. After washing, standards, controls and urine samples are pipetted into the wells followed by addition of a solution of the monoclonal antibody. The wells are washed, and a solution of peroxidase-conjugated anti-mouse immunoglobulin (rabbit) is added to the wells. Following the second washing step, a chromogenic substrate is added to all wells and the colour reaction is stopped with sulphuric acid and the absorbance is measured. Additional examples regarding how to assay CTX-II using ELISA are described in Christgau (2001 *Bone* 29:209, incorporated by reference herein.

In one embodiment, an immunoassay for determining the level of synovitis biomarker MMP-3 in human serum is performed. Methods for assaying MMP-3 as a synovitis biomarker are known in the art, and are described, for example, in Tamarat et al. (2003) *PNAS* 100: 8555. In addition, commercial kits available to test MMP-3 protein levels include the Human Matrix Metalloproteinase-3 Biotrak ELISA system (Amersham) (see also Yang et al. (2004) *Arthritis and Rheumatism* 51:691). Additional examples describing how to assay MMP-3 protein are described in Chen et al. (2006) *Rheumatology* 45:414.

In one embodiment, antibodies, or antibody fragments, are used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

Other standard methods using antibodies to detect and quantitate collagen degradation and/or synovitis markers include, but are not limited to, radioimmunoassays ("RIA"), receptor assays, enzyme immunoassays ("EIA"), cytochemical bioassays, ligand assays, immunoradiometric assays, fluoroimmunoassays, and enzyme-linked immunosorbent assays ("ELISA"). A further method includes, for ease of detection, and its quantitative nature, the sandwich or double antibody assay, of which a number of variations exist, all of which are intended to be encompassed by the present invention. These methods are well known and will be understood by those skilled in the art to require a reasonable amount of experimentation to optimize the interaction between antibodies and antigens and the detection of the antigens by the antibodies. These and other immunoassay techniques may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays known in the art and described herein to determine levels of biomarkers, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In a one embodiment, the antibody is labeled, e.g. a radiolabeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a cartilage degradation or synovitis biomarker protein.

In one embodiment of the invention, proteomic methods, e.g., mass spectrometry, are used for detecting and quantitating cartilage degradation or synovitis biomarker. For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to detect and quantitate cartilage degradation or synovitis biomarker. Mass spectrometric methods are described in, for example, U.S. Pat. Nos. 5,622,824, 5,605,798 and 5,547,835, the entire contents of each of which are incorporated herein by reference.

RNA

In one embodiment, the level of an mRNA encoding said biomarker can be measured using methods known to those skilled in the art, e.g. Northern analysis. Gene expression of the biomarker can be detected at the RNA level. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., Nuc. Acids Res. 12:7035), Northern blotting and In Situ hybridization. Gene expression can also be detected by microarray analysis as described below.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

Nuclease Protection Assays (including both ribonuclease protection assays and S1 nuclease assays) provide an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. NPAs allow the simultaneous detection of several RNA species.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification (TAS) methods have been described in the literature, for example, general reviews of these methods in Landegren, U. et al., Science 242:229-237 (1988) and Lewis, R., Genetic Engineering News 10:1, 54-55 (1990). PCR is a nucleic acid amplification method common in the art and described inter alia in U.S. Pat. Nos. 4,683,195 and 4,683,202. PCR can be used to amplify any known nucleic acid in a diagnostic context (Mok et al., 1994, Gynaecologic Oncology 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, Proc. Natl. Acad. Sci. USA 87:1874). Ligation amplification reaction or ligation amplification system uses DNA ligase and four oligonucleotides, two per target strand. This technique is described by Wu, D. Y. and Wallace, R. B., 1989, Genomics 4:560. In the Q.beta. Replicase technique, RNA replicase for the bacteriophage Q.beta., which replicates single-stranded RNA, is used to amplify the target DNA, as described by Lizardi et al., 1988, Bio/Technology 6:1197. Quantitative PCR (Q-PCR) is a technique which allows relative amounts of transcripts within a sample to be determined.

III. TNF Inhibitors

This invention describes a method for determining the efficacy of a TNFα inhibitor, e.g., a human TNFα antibody, or an antigen-binding portion thereof, for treating ankylosing spondylitis (AS). The invention also provides a method of monitoring the efficacy of a TNFα inhibitor, e.g., a human TNFα antibody, or an antigen-binding portion thereof, for decreasing the progression of structural damage associated with ankylosing spondylitis (AS) in a patient. The invention further includes a method for predicting the efficacy of a TNFα inhibitor, e.g., a human TNFα antibody, or an antigen-binding portion thereof, for the treatment of AS in a patient. Compositions and kits relating to the claimed methods are also contemplated as part of the invention.

In one embodiment, these methods include determining efficacy of isolated human antibodies, or antigen-binding portions thereof, that bind to human TNFα with high affinity and a low off rate, and have a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® and adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) Br. *J. Rheumatol.* 34:334-342).

In one embodiment, the method of the invention includes determining the efficacy of D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity, for the treatment of AS. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1 \times 10^{-8}$ M or less, even more preferably with an IC$_{50}$ of $1 \times 10^{-9}$ M or less and still more preferably with an IC$_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to methods predicting a patient's response to a treatment for AS, wherein the treatment comprises administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the invention provides methods of determining the efficacy of a treatment for AS comprising administration of an isolated human antibody, or antigen-binding portion thereof. The antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα with a $K_{off}$ of $1 \times 10^{-4}$ s$^{-1}$ or less.

In yet another embodiment, the invention provides methods of determining the efficacy of a treatment for AS comprising administration of an isolated human antibody, or antigen-binding portion thereof. The antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa$I human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H$3 human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the invention provides methods of determining the efficacy of a treatment of AS, wherein the treatment comprises the administration of an isolated human antibody, or antigen-binding portion thereof. The antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, t the invention provides methods of determining the efficacy of a treatment for AS, wherein the treatment comprises administration of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In another embodiment, the method of the invention includes determining the efficacy of a treatment for AS, wherein the treatment comprises administering a TNFα inhibitor, including, but not limited to, an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Other examples include etanercept (described in WO 91/03553 and WO 09/406476), soluble TNF receptor Type I, a pegylated soluble TNF receptor Type I (PEGs TNF-R1), or p55TNFR1gG (Lenercept). In another embodiment, the TNFα inhibitor is a recombinant TNF binding protein (r-TBP-I) (Serono).

The TNFα antibody used in the methods and compositions of the invention may be modified for improved treatment of AS. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl-CIO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat AS by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods or compositions of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection.

Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et. al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human antibodies with high affinity and a low off rate constant for hTNFα are also described in U.S. Pat. Nos. 6,090,382, 6,258,562, and 6,509,015, each of which is incorporated by reference herein.

IV. Spondyloarthropathies

TNFα has been implicated in the pathophysiology of a wide variety of disorders, including inflammatory diseases such as spondyloarthopathies (see e.g., Moeller et al. (1990) *Cytokine* 2:162; U.S. Pat. No. 5,231,024; European Patent Publication No. 260 610).

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include ank/ank transgenic mice, HLA-B27 transgenic rats (see Taurog et al. (1998) *The Spondylarthritides*. Oxford:Oxford University Press).

The methods of the invention can also be used to treat for subjects who have or are at risk of developing a spondyloarthropathy. Examples of subjects who are at risk of having spondyloarthropathies include humans suffering from arthritis. Spondyloarthropathies can be associated with other forms of arthritis, including rheumatoid arthritis. In one embodiment of the invention, biomarker levels of cartilage degradation and/or synovitis biomarkers of a patient having a spondyloarthropathy or at risk for developing a spondyloarthropathy, are determined and used to assess whether the patient is at risk for developing a spondyloarthropathy. Examples of spondyloarthropathies which can be treated with a TNFα antibody, and, accordingly, examined using the methods described herein, are described below:

1. Ankylosing Spondylitis (AS)

Tumor necrosis factor has been implicated in the pathophysiology of ankylosing spondylitis (AS) (see Verjans et al. (1991) *Arthritis Rheum.* 34:486; Verjans et al. (1994) *Clin Exp Immunol.* 97:45; Kaijtzel et al. (1999) *Hum Immunol.* 60:140). AS is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting* Abstract). Accordingly, methods of the invention can be used to provide improved treatment for AS by providing a method for determining the efficacy of a treament comprising administration of a TNF inhibitor.

In one embodiment, the method of the invention is used to determine the efficacy of administration of a TNF inhibitor for the treatment of a spondyloarthropathy, including AS, associated with IBD.

AS is often treated with nonsteroidal anti-inflammatory medications (NSAIDs), such as aspirin or indomethacin. Accordingly, the methods of the invention may be used to determine the efficacy a treatment comprising a TNFα antibody administered in combination with agents commonly used to reduce inflammation and pain commonly associated with ankylosing spondylitis.

2. Psoriatic Arthritis

Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic arthritis or psoriasis associated with the skin, refers to chronic inflammatory arthritis which is associated with psoriasis, which is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. Accordingly, the efficacy of a TNFα antibody, or antigen-binding fragment thereof, for the treatment of PsA can be determined using the method and compositions of the invention.

PsA is sometimes associated with arthritis mutilans. Arthritis mutilans refers to a disorder which is characterized by excessive bone erosion resulting in a gross, erosive deformity which mutilates the joint. In one embodiment, the efficacy of a TNFα antibody, or antigen-binding fragment thereof, for the treatment of arthritis mutilans can be determined using the method and compositions of the invention.

3. Reactive Arthritis/Reiter's Syndrome

Tumor necrosis factor has been implicated in the pathophysiology of reactive arthritis, which is also referred to as Reiter's syndrome (Braun et al. (1999) *Arthritis Rheum.* 42(10):2039). Reactive arthritis (ReA) refers to arthritis which complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including *chlamydia, campylobacter, salmonella,* or *yersinia.* In one embodiment, the efficacy of a TNFα antibody, or antigen-binding fragment thereof, for the treatment of ReA can be determined using the method and compositions of the invention.

4. Undifferentiated Spondyloarthropathies

In one embodiment, antibodies obtained using methods of the invention are used to treat subjects suffering from undifferentiated spondyloarthropathies (see Zeidler et al. (1992) *Rheum Dis Clin North Am.* 18:187). Other terms used to describe undifferentiated spondyloarthropathies include seronegative oligoarthritis and undifferentiated oligoarthritis. Undifferentiated spondyloarthropathies, as used herein, refers to a disorder wherein the subject demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS. In one embodiment, the efficacy of a TNFα antibody, or antigen-binding fragment thereof, for the treatment of undifferentiated spondyloarthropathies can be determined using the method and compositions of the invention.

V. Pharmaceutical Compositions and Pharmaceutical Administration

A. Compositions and Administration

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, an antibody or antibody portion for use in the methods of the invention is coformulated with and/or coadministered with one or more additional therapeutic agents, including an AS inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of a TNFα inhibitor and a pharmaceutically acceptable carrier, wherein the effective amount of the TNFα inhibitor may be effective to treat AS. In one embodiment, the antibody or antibody portion for use in the methods of the invention is incorporated into a pharmaceutical formulation as described in PCT/IB03/04502 and U.S. application Ser. No. 10/222,140, incorporated by reference herein. This formulation includes a concentration 50 mg/ml of the antibody D2E7, wherein one pre-filled syringe contains 40 mg of antibody for subcutaneous injection. In another embodiment, the formulation of the invention includes D2E7.

The antibodies, antibody-portions, and other TNFα inhibitors of the present invention can be administered by a variety of methods known in the art, although for many therapeutic applications, the preferred route/mode of administration is subcutaneous injection. In another embodiment, administration is via intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

The TNFα antibodies used in the invention can also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, incorporated by reference herein, are used to treat rheumatoid arthritis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In one embodiment, the invention provides a single dose method for treating a TNFα related disorder, comprising administering to a subject in need thereof a single dose of a TNFα inhibitor, such as a human antibody. In one embodiment, the TNFα inhibitor is the anti-TNFα antibody D2E7. The single dose of TNFα inhibitor can be any therapeutically or prophylactically effective amount. In one embodiment, a subject is administered either a 20 mg, a 40 mg, or an 80 mg single dose of D2E7. The single dose may be administered through any route, including, for example, subcutaneous administration. Biweekly dosing regimens can be used to treat disorders in which TNFα activity is detrimental, and are further described in U.S. application Ser. No. 10/163,657. Multiple variable dose methods of treatment or prevention can also be used to treat disorders in which TNFα activity is detrimental, and are further described in PCT appln. no. PCT/US05/12007.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention also pertains to packaged pharmaceutical compositions or kits for administering the anti-TNF antibodies of the invention for the treatment of AS. In one embodiment of the invention, the kit comprises a TNFα inhibitor, such as an antibody, an second pharmaceutical composition comprising an additional therapeutic agent, and instructions for administration for treatment of AS. The instructions may describe how, e.g., subcutaneously, and when, e.g., at week 0 and week 2, the different doses of TNFα inhibitor and/or the additional therapeutic agent shall be administered to a subject for treatment.

Another aspect of the invention pertains to kits containing a pharmaceutical composition comprising an anti-TNFα antibody and a pharmaceutically acceptable carrier and one or more pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits contain instructions for dosing of the pharmaceutical compositions for the treatment of a TNFα related disorder. In one embodiment, the contains instructions regarding how to determine the efficacy of the TNF inhibitor for the treatment of AS. The kit may include any of the following for performing the methods of the invention: a detectable agent that specifically recognizes CTX-II and/or MMP-3; instructions for use; and reagents for isolating a sample from the patient.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

B. Additional Therapeutic Agents

The invention pertains to determining the efficacy of a TNF inhibitor for the treatment of AS, alone or in combination with an additional therapeutic agent. The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions. In certain embodiments, an antibody or antibody portion of the invention is coformulated with and/or coadministered with one or more additional therapeutic agents that are useful for treating a TNFα related disorder. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies.

Nonlimiting examples of therapeutic agents with which an antibody, antibody portion, or other TNFα inhibitor can be combined in a method of treatment and assessed according to the methods of the invention include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-IRA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.-Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα antibody of the invention to treat an TNFα-related disorder using the multiple variable dose or single dose method of treatments of the invention.

In one embodiment, the invention includes an article of manufacture or a method of treatment for determining the efficacy of a TNF inhibitor in combination with one of the following agents for the treatment of a TNFα-related disorder in which TNFα activity is detrimental: anti-IL12 antibody (ABT 874); anti-IL18 antibody (ABT 325); small molecule inhibitor of LCK; small molecule inhibitor of COT; anti-IL1 antibody; small molecule inhibitor of MK2; anti-CD19 antibody; small molecule inhibitor of CXCR3; small molecule inhibitor of CCR5; small molecule inhibitor of CCR11 anti-E/L selectin antibody; small molecule inhibitor of P2X7; small molecule inhibitor of IRAK-4; small molecule agonist of glucocorticoid receptor; anti-C5a receptor antibody; small molecule inhibitor of C5a receptor; anti-CD32 antibody; and CD32 as a therapeutic protein.

In yet another embodiment, the invention includes an article of manufacture or a method of treatment for determining the efficacy of a TNF inhibitor in combination with an antibiotic or antiinfective agent. Antiinfective agents include those agents known in the art to treat viral, fungal, parasitic or bacterial infections. The term, "antibiotic," as used herein, refers to a chemical substance that inhibits the growth of, or kills, microorganisms. Encompassed by this term are antibiotic produced by a microorganism, as well as synthetic antibiotics (e.g., analogs) known in the art. Antibiotics include, but are not limited to, clarithromycin (Biaxin®), ciprofloxacin (Cipro®), and metronidazole (Flagyl®).

In another embodiment, the invention includes an article of manufacture or a method of treatment for determining the efficacy of a TNF inhibitor in combination with a drug used to treat Crohn's disease or a Crohn's-related disorder. Examples of therapeutic agents which can be used to treat Crohn's include mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, hyoscyamine sulfate, cholestyramine/sucrose, ciprofloxacin hydrochloride, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, natalizumab, methylprednisolone, interferon-gamma, and sargramostim (GM-CSF). In one embodiment, methotrexate is administered for the treatment of Crohn's disease at a dose of 2.5 mg to 30 mg per week.

The TNFα antibody may be administered in combination with topical orticosteroids, vitamin D analogs, and topical or oral retinoids, or combinations thereof, for the treatment of psoriasis. In addition, the TNFα antibody may be administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB and other phototherapy, and sulfasalazine.

In one embodiment, the TNFα antibody of the invention is administered using a multiple-variable dose method for the treatment of AS in combination with one of the above mentioned agents for the treatment of an intestinal disorder. In another embodiment, the above-mentioned additional agents are used in combination with a TNFα antibody in the single dose method of treatment of the invention. In still another embodiment, the TNFα antibody is administered on a biweekly dosing regimen.

Any one of the above-mentioned therapeutic agents, alone or in combination therewith, can be administered to a subject suffering from a TNFα-related disorder in which TNFα is detrimental, in combination with the TNFα antibody using a multiple variable dose treatment regimen. In one embodiment, any one of the above-mentioned therapeutic agents, alone or in combination therewith, can be administered to a subject suffering from an intestinal disorder in addition to a TNFα antibody to treat another TNFα-related disorder, such as rheumatoid arthritis. It should be understood that the additional therapeutic agents can be used in combination therapy as described above, but also may be used in other indications described herein wherein a beneficial effect is desired.

The present invention is further illustrated by the following example which should not be construed as limiting in any way.

EXAMPLE

Adalimumab Suppresses Biomarkers of Cartilage Degradation and Synovitis in Active Ankylosing Spondylitis (AS)

The objective of the following study was to analyze potential biomarkers of cartilage and bone destruction e.g., bone resorption markers, collagen degradation markers, and synovitis markers, in a controlled trial of adalimumab in the treatment of moderate to severe AS. The study also sought to analyze the effect of a TNF inhibitor, i.e., adalimumab, on the correlation of a bone resorption marker, a collagen degradation marker, and a synovitis marker to CRP, a known marker for AS, in an AS study population.

Methods

Patients with active AS who had an inadequate response to at least one NSAID or DMARD were eligible to enroll in this study. The study design is depicted in FIG. 1. Patients were randomized to receive either placebo or adalimumab 40 mg subcutaneously (sc) every other week (eow) during an initial 24-week double-bind period, followed by an 80-week open label period. Three biomarkers were analyzed at baseline and after treatment with adalimumab or placebo at 12 and 24 weeks. Specifically, the bone resorption marker, serum Type I collagen N-telopeptides (NTX), the collagen degradation biomarker, urinary Type II collagen C-telopeptides (urinary CTX-II), and the synovitis biomarker, serum matrix metalloprotease 3 (MMPS) were analyzed. Thus, primary efficacy parameters included ASsessment in AS (ASAS) Working Group criteria, the Bath AS Disease Activity Index (BASDAI), and CRP. By ELISA, concentrations of urinary Type II collagen C-telopeptides (urinary CTX-II), serum Type I collagen N-telopeptides (NTX), and serum MMP3 were measured for each patient at baseline, and 12 and 24 weeks. Concentration differences from baseline in each treatment group were determined, as well as correlations between changes in these biomarkers and other AS outcomes.

The patient inclusion criteria included the following: patients ≧18 years old; active AS, defined by fulfillment of at least 2 of the following 3 criteria: (1) BASDAI score ≧4, (2) Visual Analog Scale (VAS) score for Total Back Pain ≧4, and (3) Morning stiffness ≧1 hour; and inadequate response to at least one NSAID.

Patient exclusion criteria included the following: previously received anti-TNF treatment; radiological evidence of total spinal ankylosis (bamboo spine); use of previous DMARD within 4 weeks of baseline (other than methotrexate, sulfasalazine, or hydroxychloroquine); intra-articular joint injection with corticosteroids within 4 weeks of baseline; and use of other biologics or investigational therapy within 6 weeks of baseline.

Results

A total of 82 patients were enrolled: 44 placebo patients vs. 38 adalimumab patients. Of the 82 total patients, 80 (98%) of patients completed the 24 week period. The two patients who did not complete the 24 week period were from the placebo group. Baseline characteristics were similar between treatment groups. Baseline demographics are shown in Table 1 below.

TABLE 1

Baseline Demographics.

| | Placebo (N = 44) | Adalimumab 40 mg eow (N = 38) |
|---|---|---|
| Age (years)† | 40.0 | 41.9 |
| Race (% Caucasian) | 42 (95.5) | 37 (97.4) |
| Sex (% male) | 36 (81.8) | 29 (76.3) |
| Weight (kg) † | 78.2 | 76.1 |
| Duration of AS (years) † | 12.1 | 14.5 |
| CRP (mg/dL) † | 2.3 | 1.8 |

TABLE 1-continued

Baseline Demographics.

|  | Placebo (N = 44) | Adalimumab 40 mg eow (N = 38) |
|---|---|---|
| NTX (nm/bce) † | 9.77 | 10.5 |
| Urinary CTX-II concentration (ng/ml) | 388.2 | 324.8 |
| MMP-3 (ng/ml) † | 57.1 | 25.3 |

Among all patients in the study, CRP levels were significantly correlated to levels of urinary CTX-II, MMP3 and NTX at baseline. The correlation between CRP and urinary CTX-II levels was higher than the correlation between CRP and MMP3 and NTX levels. Biomarker and CRP correlations at baseline are shown in Table 2 below.

TABLE 2

Biomarker and CRP correlations at baseline.

| All patients at baseline | r = correlation value (N, p-value) | | |
|---|---|---|---|
|  | Urinary CTX-II | MMP3 | NTX |
| CRP | 0.71 (80, <0.001) | 0.45 (81, <0.001) | 0.37 (80, 0.001) |
| Urinary CTX-II | — | 0.27 (79, 0.015) | 0.49 (78, <0.001) | r = correlation value
N = patients

Significant reductions in urinary CTX-II and MMP3 concentrations (shown below in Table 3) occurred in adalimumab vs. placebo pts at 12 and 24 wks (p<0.001), but there were no significant differences for NTX.

TABLE 3

Significant reductions in urinary CTX-II and MMP3.

| Biomarker | Visit | Change in Adalimumab(%) | Change in Placebo (%) |
|---|---|---|---|
| Urinary CTX-II | 12-Week | −76.8 (−9.6) | 43.8 (22.2) |
|  | 24-Week | −64.7 (3.2) | 47.4 (29.8) |
| MMP3 | 12-Week | −3.9 (−12.3) | 12.4 (18.9) |
|  | 24-Week | −3.2 (−8.6) | 12.5 (20.1) |

Figure 2:
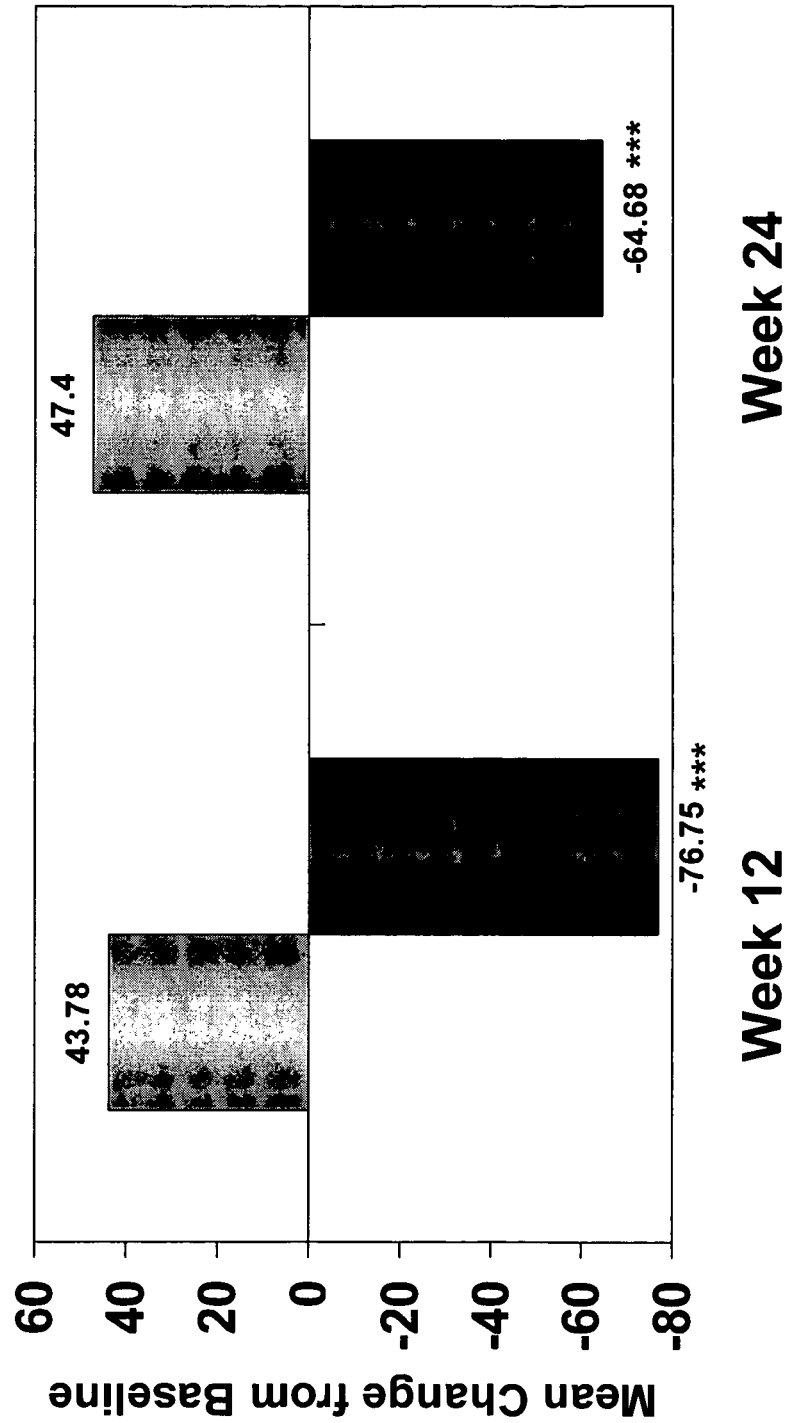
FIG. 2 shows a graph which indicates that alimumab patients experienced significant reductions in urinary CTX-II levels versus placebo at week 12 and week 24.

As shown in FIG. 2, adalimumab patients experienced significant reductions in urinary CTX-II levels versus placebo at Week 12 and Week 24. Adalimumab patients also experienced statistically significant reductions in MMP3 levels versus placebo patients at 12 weeks and 24 weeks, as shown in FIG. 3. CRP levels were significantly reduced in adalimumab patients compared to placebo patients at week 12 and week 24 (see FIG. 4).

Changes in CRP, urinary CTX-II, and MMP-3 levels from baseline to week 12 were statistically significantly correlated in the adalimumab group. Significant correlations were noted between baseline CRP and 1) urinary CTX-II (r=0.71), 2) MMP3 (r=0.45), and 3) NTX (r=0.37) (p≦0.001), and between urinary CTX-II and NTX (r=0.49; p<0.0001). Twelve-week changes in urinary CTX-II and MMP3 correlated significantly with changes in CRP (r=0.40 and 0.43, respectively) (p≦0.005). In addition, the 12-week change in urinary CTX-II correlated significantly with the change in MMP3 (r=0.41, p<0.0001). In the adalimumab group, the correlation analysis confirms that improvement in CRP levels is associated with reduction in both urinary CTX-II and MMP-3 levels. Correlations between CRP and biomarker change from baseline at week 12 are shown below in Table 2.

TABLE 4

Correlations Between CRP and Biomarker Change from Baseline at Week 12*

|  | R = correlation value (N, p-value†) | | |
|---|---|---|---|
|  | Urinary CTX-II | MMP3 | NTX |
| Placebo |  |  |  |
| CRP | 0.21 (42, 0.172) | 0.34 (44, 0.023) | 0.08 (43, 0.629) |
| Urinary CTX-II | — | 0.45 (42, 0.003) | 0.27 (41, 0.089) |
| Adalimumab |  |  |  |
| CRP | 0.41 (38, 0.010) | 0.37 (37, 0.024) | 0.08 (37, 0.620) |
| Urinary CTX-II | — | 0.15 (37, 0.375) | 0.10 (37, 0.540) |

In conclusion, in patients with moderate to severe AS, adalimumab significantly suppressed biomarkers that reflect synovitis and cartilage matrix degradation. Adalimumab induced suppression of the biomarkers that reflect synovitis (MMP3) and cartilage matrix degradation (urinary CTX-II), suggesting that adalimumab slows down structural damage associated with AS. In addition, changes in urinary CTX-II and MMP3 were significantly correlated with change in CRP.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method for determining the efficacy of a human anti-TNFα antibody, or an antigen-binding portion thereof, for treating a subject having ankylosing spondylitis (AS), said method comprising
determining a level of a collagen degradation biomarker and a synovitis biomarker in a sample(s) obtained from the subject following administration of the human anti-TNFα antibody, or an antigen-binding portion thereof; and
comparing the level of the collagen degradation biomarker and the synovitis biomarker in the sample(s) obtained from the subject with a known standard level of the collagen degradation biomarker and the synovitis biomarker associated with AS, wherein a lower level of the collagen degradation biomarker and the synovitis biomarker in the sample(s) from the subject relative to the known standard level of the collagen degradation biomarker and the synovitis biomarker indicates that the human anti-TNFα antibody, or an antigen-binding portion thereof, is efficacious for the treatment of AS in the subject.

2. The method of claim 1, wherein the collagen degradation biomarker is type II collagen C-telopeptide (CTX-II).

3. The method of claim 2, wherein the collagen degradation biomarker is urinary type II collagen C-telopeptide (CTX-II).

4. The method of claim 1, wherein the synovitis biomarker is matrix metalloprotease 3 (MMP3).

5. The method of claim 4, wherein the synovitis biomarker is serum metalloprotease 3 (MMP3).

6. The method of claim 1, further comprising
determining a level of C-reactive protein (CRP) in a sample obtained from the subject following administration of the human anti-TNFα antibody, or an antigen-binding portion thereof; and
comparing the level of CRP in the sample with a known standard CRP level associated with AS, wherein a lower level of CRP in the sample relative to the known standard level of CRP indicates that the human anti-TNFα antibody, or an antigen-binding portion thereof, is efficacious for the treatment of AS in the subject.

7. A method for determining the efficacy of a human anti-TNFα antibody, or an antigen-binding portion thereof, for treating a subject having ankylosing spondylitis (AS), said method comprising
determining a level of a collagen degradation biomarker and a synovitis biomarker in a sample(s) obtained from the subject following administration of the human anti-TNFα antibody, or antigen-binding portion thereof; and
comparing the level of the collagen degradation biomarker and the synovitis biomarker in the sample(s) to a baseline level of the collagen degradation biomarker and the synovitis biomarker, wherein a lower level of the collagen degradation biomarker and the synovitis biomarker in the sample(s) relative to the baseline level of the collagen degradation biomarker and the synovitis biomarker indicates that the human anti-TNFα antibody, or an antigen-binding portion thereof, is efficacious for the treatment of AS in the subject.

8. The method of claim 7, wherein the collagen degradation biomarker is type II collagen C-telopeptide (CTX-II).

9. The method of claim 8, wherein the collagen degradation biomarker is urinary type II collagen C-telopeptide (CTX-II).

10. The method of claim 7, wherein the synovitis biomarker is matrix metalloprotease 3 (MMP3).

11. The method of claim 10, wherein the synovitis biomarker is serum metalloprotease 3 (MMP3).

12. The method of claim 1 or 7, wherein the level of the biomarker is determined by performing an ELISA.

13. A method for determining the efficacy of a human anti-TNFα antibody, or an antigen-binding portion thereof, for the treatment of ankylosing spondylitis (AS) in a subject having AS, said method comprising
determining level of type II collagen C-telopeptide (CTX-II) in a sample from the subject following treatment with the human anti-TNFα antibody, or an antigen-binding portion thereof, and
comparing the level of CTX-II in the sample with a baseline level of CTX-II from the subject having AS, wherein a decrease in the level of the CTX-II in the sample of at least 9% relative to the baseline level of CTX-II indicates that the human anti-TNFα antibody, or an antigen-binding portion thereof, is effective for the treatment of AS in the subject.

14. The method of claim 13, wherein the CTX-II is urinary CTX-II.

15. The method of claim 13, wherein the level of CTX-II is determined by performing an ELISA.

16. A method of determining the efficacy of a human anti-TNFα antibody, or antigen-binding portion thereof, for the treatment of ankylosing spondylitis (AS) in a subject having AS, said method comprising
determining a level of type II collagen C-telopeptide (CTX-II) in a sample obtained from the subject following administration of the anti-human TNFα antibody, or antigen-binding portion thereof, and comparing the level of CTX-II in the sample with a known standard level of CTX-II associated with AS, wherein a decrease in the level of CTX-II in the sample of at least 9% relative to the known standard level of CTX-II indicates that the human anti-TNFα antibody, or antigen-binding portion thereof, is effective for the treatment of AS in the subject.

17. A method for determining the efficacy of a human anti-TNFα antibody, or an antigen-binding portion thereof, for treating ankylosing spondylitis (AS) in a subject having AS, said method comprising determining levels of type II collagen C-telopeptide (CTX-II) and matrix metalloprotease 3 (MMP3) in a sample(s) obtained from the subject having AS following administration of the human anti-TNFα antibody, or an antigen-binding portion thereof, and comparing the levels of CTX-II and MMP3 in the sample(s) with known standard levels of CTX-II and MMP3 associated with AS, wherein lower CTX-II and MMP3 levels in the sample(s) from the subject relative to the known standard levels of CTX-II and MMP3 indicates that the human anti-TNFα antibody, or an antigen-binding portion thereof, is effective at decreasing structural damage associated with AS in the patient.

18. The method of claim 16 or 17, wherein the CTX-II is urinary CTX-II.

19. The method of claim 16 or 17, wherein the CTX-II level is determined by performing an ELISA.

20. The method of any one of claims 1, 7, 13, 16, or 17, wherein the human anti-TNFα antibody, or antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

21. The method of any one of claims 1, 7, 13, 16, or 17, wherein the human anti-TNFα antibody, or antigen-binding portion thereof, has the following characteristics:
a) dissociates from human TNFα with a $K_{off}$ rate constant of $1 \times 10^{-3}$ s$^{-1}$ or less, as determined by surface plasmon resonance;
b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

22. The method of any one of claims 1, 7, 13, 16, or 17, wherein the human anti-TNFα antibody, or antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

23. The method of any one of claims 1, 7, 13, 16, or 17, wherein the human anti-TNFα antibody, or antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

24. The method of any one of claims 1, 7, 13, 16, or 17, wherein the human anti-TNFα antibody, or antigen-binding portion thereof, is adalimumab.

25. The method of any one of claims 1, 7, 13, 16, or 17, wherein the human TNFα antibody, or antigen-binding portion thereof, is golimumab.

26. A method for determining the efficacy of a TNFα antibody, or an antigen-binding portion thereof, for treating a subject having ankylosing spondylitis (AS), said method comprising determining a level of a collagen degradation biomarker and a synovitis biomarker in a sample(s) obtained from the subject following administration of the TNFα antibody, or an antigen-binding portion thereof; and comparing the level of the collagen degradation biomarker and the synovitis biomarker in the sample(s) obtained from the subject with a known standard level of the collagen degradation biomarker and the synovitis biomarker associated with AS, wherein a lower level of the collagen degradation biomarker and the synovitis biomarker in the sample(s) from the subject relative to the known standard level of the collagen degradation biomarker and the synovitis biomarker indicates that the TNFα antibody, or an antigen-binding portion thereof, is efficacious for the treatment of AS in the subject.

27. The method of claim 26, wherein the collagen degradation biomarker is type II collagen C-telopeptide (CTX-II).

28. The method of claim 26, wherein the synovitis biomarker is matrix metalloprotease 3 (MMP3).

29. The method of claim 26, further comprising determining a level of C-reactive protein (CRP) in a sample obtained from the subject following administration of the TNFα antibody, or an antigen-binding portion thereof; and comparing the level of CRP in the sample with a known standard CRP level associated with AS, wherein a lower level of CRP in the sample relative to the known standard level of CRP indicates that the TNFα antibody, or an antigen-binding portion thereof, is efficacious for the treatment of AS in the subject.

30. A method for determining the efficacy of a TNFα antibody, or an antigen-binding portion thereof, for treating a subject having ankylosing spondylitis (AS), said method comprising determining a level of a collagen degradation biomarker and a synovitis biomarker in a sample(s) obtained from the subject following administration of the TNFα antibody, or antigen-binding portion thereof; and comparing the level of the collagen degradation biomarker and the synovitis biomarker in the sample(s) to a baseline level of the collagen degradation biomarker and the synovitis biomarker, wherein a lower level of the collagen degradation biomarker and the synovitis biomarker in the sample(s) relative to the baseline level of the collagen degradation biomarker and the synovitis biomarker indicates that the TNFα antibody, or an antigen-binding portion thereof, is efficacious for the treatment of AS in the subject.

31. The method of claim 30, wherein the collagen degradation biomarker is urinary type II collagen C-telopeptide (CTX-II).

32. The method of claim 30, wherein the synovitis biomarker is serum metalloprotease 3 (MMP3).

33. A method for determining the efficacy of a TNFα antibody, or an antigen-binding portion thereof, for the treatment of ankylosing spondylitis (AS) in a subject having AS, said method comprising determining level of type II collagen C-telopeptide (CTX-II) in a sample from the subject following treatment with the TNFα antibody, or an antigen-binding portion thereof, and comparing the level of CTX-II in the sample with a baseline level of CTX-II from the subject having AS, wherein a decrease in the level of the CTX-II in the sample of at least 9% relative to the baseline level of CTX-II indicates that the TNFα antibody, or an antigen-binding portion thereof, is effective for the treatment of AS in the subject.

34. A method of determining the efficacy of a TNFα antibody, or antigen-binding portion thereof, for the treatment of ankylosing spondylitis (AS) in a subject having AS, said method comprising determining a level of type II collagen C-telopeptide (CTX-II) in a sample obtained from the subject following administration of the TNFα antibody, or antigen-binding portion thereof, and comparing the level of CTX-II in the sample with a known standard level of CTX-II associated with AS, wherein a decrease in the level of CTX-II in the sample of at least 9% relative to the known standard level of CTX-II indicates that the TNFα antibody, or antigen-binding portion thereof, is effective for the treatment of AS in the subject.

35. A method for determining the efficacy of a TNFα antibody, or an antigen-binding portion thereof, for treating ankylosing spondylitis (AS) in a subject having AS, said method comprising determining levels of type II collagen C-telopeptide (CTX-II) and matrix metalloprotease 3 (MMP3) in a sample(s) obtained from the subject having AS following administration of the TNFα antibody, or an antigen-binding portion thereof, and comparing the levels of CTX-II and MMP3 in the sample(s) with known standard levels of CTX-II and MMP3 associated with AS, wherein lower CTX-II and MMP3 levels in the sample(s) from the subject relative to the known standard levels of CTX-II and MMP3 indicates that the TNFα antibody, or an antigen-binding portion thereof, is effective at decreasing structural damage associated with AS in the patient.

36. The method of any one of claims 33, 34, or 35, wherein the level of CTX-II is determined by performing an ELISA.

37. A method for determining the efficacy of a TNFα antibody, or an antigen-binding portion thereof, for treating ankylosing spondylitis (AS) in a subject having AS, said method comprising determining levels of type II collagen C-telopeptide (CTX-II) and matrix metalloprotease 3 (MMP3) in a sample(s) obtained from the subject having AS following administration of the human anti-TNFα antibody, or an antigen-binding portion thereof, and comparing the levels of CTX-II and MMP3 in the sample(s) with baseline levels of CTX-II and MMP3 associated with AS, wherein lower CTX-II and MMP3 levels in the sample(s) from the subject relative to the baseline levels of CTX-II and MMP3 indicates that the anti-TNFα antibody, or an antigen-binding portion thereof, is effective at decreasing structural damage associated with AS in the patient.

38. The method of any one of claims 26, 30, 33-35, or 37, wherein the TNFα antibody, or an antigen-binding portion thereof, is infliximab.

* * * * *